United States Patent
Nae et al.

(10) Patent No.: US 11,304,831 B2
(45) Date of Patent: Apr. 19, 2022

(54) SYSTEMS AND METHODS FOR MAKING ENCAPSULATED HOURGLASS SHAPED STENTS

(71) Applicant: V-Wave Ltd., Caesarea (IL)

(72) Inventors: Nir Nae, Binyamina (IL); Lior Rosen, Or Akiva (IL); Neal Eigler, Agoura Hills, CA (US); Erez Rozenfeld, Shoham (IL); Werner Hafelfinger, Thousand Oaks, CA (US); Yeela Scop, Tel Aviv (IL)

(73) Assignee: V-Wave Ltd., Caesarea (IL)

( * ) Notice: Subject to any disclaimer, the term of this patent is extended or adjusted under 35 U.S.C. 154(b) by 0 days.

(21) Appl. No.: 17/095,615

(22) Filed: Nov. 11, 2020

(65) Prior Publication Data

US 2021/0100665 A1    Apr. 8, 2021

Related U.S. Application Data

(60) Continuation of application No. PCT/IB2019/060257, filed on Nov. 27, 2019, and a
(Continued)

(51) Int. Cl.
*A61F 2/07*    (2013.01)
*A61F 2/844*    (2013.01)
(Continued)

(52) U.S. Cl.
CPC ............ *A61F 2/844* (2013.01); *A61F 2/07* (2013.01); *A61F 2/2415* (2013.01); *A61F 2/91* (2013.01);
(Continued)

(58) Field of Classification Search
CPC .................... A61F 2/844; A61F 2/07
See application file for complete search history.

(56) References Cited

U.S. PATENT DOCUMENTS 3,852,334 A    12/1974 Dusza et al.
3,874,388 A    4/1975 King et al.
(Continued)

FOREIGN PATENT DOCUMENTS

EP    2238933 A1    10/2010
EP    2305321 A1    4/2011
(Continued)

OTHER PUBLICATIONS

U.S. Appl. No. 09/839,643 / U.S. Pat. No. 8,091,556, filed Apr. 20, 2001 / Jan. 10, 2012.
(Continued)

*Primary Examiner* — Jeffry H Aftergut
*Assistant Examiner* — Jaeyun Lee
(74) *Attorney, Agent, or Firm* — Eversheds Sutherland (US) LLP; Christopher C. Bolten; Nicola A. Pisano

(57) ABSTRACT

Systems and methods for the manufacture of an hourglass shaped stent-graft assembly having an hourglass shaped stent, graft layers, and an assembly mandrel having an hourglass shaped mandrel portion. Hourglass shaped stent may have superelastic and self-expanding properties. Hourglass shaped stent may be encapsulated using hourglass shaped mandrel assembly coupled to a dilation mandrel used for depositing graft layers upon hourglass shaped mandrel assembly. Hourglass shaped mandrel assembly may have removably coupled conical portions. The stent-graft assembly may be compressed and heated to form a monolithic layer of biocompatible material. Encapsulated hourglass shaped stents may be used to treat subjects suffering from heart failure by implanting the encapsulated stent securely in the atrial septum to allow blood flow from the left atrium to the right atrium when blood pressure in the left atrium exceeds that on the right atrium. The encapsulated stents may also be used to treat pulmonary hypertension.

24 Claims, 19 Drawing Sheets

Related U.S. Application Data division of application No. 16/205,213, filed on Nov. 29, 2018, now Pat. No. 10,835,394, said application No. PCT/IB2019/060257 is a continuation-in-part of application No. 16/205,213, filed on Nov. 29, 2018, now Pat. No. 10,835,394, which is a continuation-in-part of application No. 15/798,250, filed on Oct. 30, 2017, now Pat. No. 11,109,988, which is a continuation of application No. 15/608,948, filed on May 30, 2017, now abandoned.

(60) Provisional application No. 62/343,658, filed on May 31, 2016.

(51) Int. Cl.
    *A61F 2/958*     (2013.01)
    *A61F 2/91*     (2013.01)
    *A61F 2/24*     (2006.01)
    *A61F 2/915*     (2013.01)

(52) U.S. Cl.
CPC ............... *A61F 2/915* (2013.01); *A61F 2/958* (2013.01); *A61F 2002/072* (2013.01); *A61F 2210/0014* (2013.01); *A61F 2210/0076* (2013.01); *A61F 2220/0041* (2013.01); *A61F 2220/0058* (2013.01); *A61F 2230/001* (2013.01); *A61F 2230/0067* (2013.01); *A61F 2230/0078* (2013.01); *A61F 2240/00* (2013.01); *A61F 2240/001* (2013.01); *A61F 2240/004* (2013.01); *A61F 2250/0039* (2013.01); *A61F 2250/0082* (2013.01)

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |

(56) References Cited

U.S. PATENT DOCUMENTS

| | | |
|---|---|---|
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,639,459 B2 | 5/2020 | Nitzan et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0137682 A1 | 6/2005 | Justino |
| 2005/0148925 A1 | 7/2005 | Rottenberg et al. |

(56) References Cited

U.S. PATENT DOCUMENTS

| | | |
|---|---|---|
| 2005/0165344 A1 | 7/2005 | Dobak, III |
| 2005/0182486 A1 | 8/2005 | Gabbay |
| 2005/0283231 A1 | 12/2005 | Haug et al. |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0191863 A1 | 8/2007 | De Juan, Jr. et al. |
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al.. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | Mcnamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0359556 A1 | 12/2015 | Vardi |
| 2016/0007924 A1 | 1/2016 | Eigler et al. |
| 2016/0022423 A1 | 1/2016 | Mcnamara et al. |
| 2016/0022970 A1 | 1/2016 | Forcucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |

(56) References Cited

U.S. PATENT DOCUMENTS

| | | | |
|---|---|---|---|
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1 | 11/2017 | Rosen et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015188 A1 | 1/2019 | Eigler et al. |
| 2019/0021861 A1 | 1/2019 | Finch |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |

FOREIGN PATENT DOCUMENTS

| | | | |
|---|---|---|---|
| EP | 1965842 B1 | 11/2011 |
| EP | 3400907 A1 | 11/2018 |
| FR | 2827153 A1 | 1/2003 |
| WO | WO-9727898 A1 | 8/1997 |
| WO | WO-9960941 A1 | 12/1999 |
| WO | WO-0044311 A2 | 8/2000 |
| WO | WO-0110314 A2 | 2/2001 |
| WO | WO-0226281 A1 | 4/2002 |
| WO | WO-02071974 A2 | 9/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2009029261 A1 | 3/2009 |
| WO | WO-2010128501 A1 | 11/2010 |
| WO | WO-2010129089 A2 | 11/2010 |
| WO | WO-2011062858 A1 | 5/2011 |
| WO | WO-2013096965 A1 | 6/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019218072 A1 | 11/2019 |

OTHER PUBLICATIONS

U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752, filed Oct. 31, 2017.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.
U.S. Appl. No. 15/668,622 / U.S. Pat. No. 10,463,490, filed Aug. 3, 2017 / Nov. 5, 2019.
U.S. Appl. No. 15/798,250, filed Oct. 30, 2017.
U.S. Appl. No. 15/988,888 / U.S. Pat. No. 10,828,151, filed May 24, 2018 / Nov. 10, 2020.
U.S. Appl. No. 16/130,978 / U.S. Pat. No. 10,251,740, filed Sep. 13, 2018 / Apr. 9, 2019.
U.S. Appl. No. 16/130,988, filed Sep. 13, 2018.
U.S. Appl. No. 16/205,213 / U.S. Pat. No. 10,835,394, filed Nov. 29, 2018 / Nov. 17, 2020.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/672,420, filed Nov. 1, 2019.
U.S. Appl. No. 16/686,013, filed Nov. 15, 2019.
U.S. Appl. No. 16/866,377, filed May 4, 2020.
U.S. Appl. No. 16/875,652, filed May 15, 2020.
U.S. Appl. No. 16/876,640, filed May 18, 2020.
U.S. Appl. No. 16/878,228, filed May 19, 2020.

(56) References Cited

OTHER PUBLICATIONS

U.S. Appl. No. 16/963,139, filed Jul. 17, 2020.
U.S. Appl. No. 17/092,063, filed Nov. 6, 2020.
U.S. Appl. No. 17/092,081, filed Nov. 6, 2020.
International Search Report & Written Opinion dated Jul. 14, 2020 in Int'l PCT Patent Appl. Serial No. PCT/IB2020/053832.
International Search Report & Written Opinion dated Aug. 12, 2020 in Int'l PCT Patent Appl. Serial No. PCT/IB2020/053118.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, http://dx.doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Ando, et al., Left ventricular decompression through a patent foramen ovale in a patient with hypertrophic cardiomyopathy: A case report, Cardiovascular Ultrasound, 2: 1-7 (2004).
Article 34 Amendments dated May 28, 2013 in Int'l PCT Patent Appl. Serial No. PCT/IB2012/001859.
Article 34 Amendments dated Nov. 27, 2012 in Int'l PCT Patent Appl. Serial No. PCT/IL2011/000958.
Ataya et al., "A Review of Targeted Pulmonary Arterial Hypertension-Specific Pharmacotherapy," J. Clin. Med., 5(12):114(2016).
"Atrium Advanta V12, Balloon Expandable Covered Stent, Improving Patient Outcomes with An Endovascular Approach," Brochure, 8 pages, Getinge (2017).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," Chest, 156(6):1176-1186 (2019).
Boehm, et al., "Balloon Atrial Septostomy: History and Technique," Images Paeditr. Cardiol., 8(1):8-14(2006).

Braunwald, Heart Disease, Chapter 6, pp. 186.
Bridges, et al., "The Society of Thoracic Surgeons Practice Guideline Series: Transmyocardial Laser Revascularization," Ann Thorac Surg., 77:1494-1502 (2004).
Bristow, et al., "Improvement in cardiac myocite function by biological effects of medical therapy: a new concept in the treatment of heart failure," European Heart Journal, 16 (Suppl.F): 20-31 (1995).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Case, et al., "Relief of High Left-Atrial Pressure in Left-Ventricular Failure," Lancet, (pp. 841-842), Oct. 17, 1964.
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Coats, et al., "Controlled Trial of Physical Training in Chronic Heart Failure: Exercise Performance, Hemodynamics, Ventilation, and Autonomic Function," Circulation, 85: 2119-2131 (1992).
Davies et al., "Abnormal left heart function after operation for atrial septal defect," British Heart Journal, 32:747-753 (1970).
Davies, et al., "Reduced Contraction and Altered Frequency Response of Isolated Ventricular Myocytes From Patients With Heart Failure, Circulation," 92: 2540-2549 (1995).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).

(56) References Cited

OTHER PUBLICATIONS

Drazner et al., "Relationship between Right and Left-Sided Filling Pressures in 1000 Patients with Advanced Heart Failure," Heart Lung Transplant, 18:1126-1132 (1999).

Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.

Eigler et al., "Cardiac Unloading with an Implantable Interatrial Shunt in Heart Failure: Serial Observations in an Ovine Model of Ischemic Cardiomyopathy," Structural Heart, 1:40-48 (2017).

Eigler, et al., Implantation and Recovery of Temporary Metallic Stents in Canine Coronary Arteries, JACC, 22(4):1207-1213 (1993).

Ennezat, et al., An unusual case of low-flow, low gradient severe aortic stenosis: Left-to-right shunt due to atrial septal defect, Cardiology, 113(2):146-148, (2009).

Eshaghian et al., "Relation of Loop Diuretic Dose to Mortality in Advanced Heart Failure," Am J Cardiol., 97:1759-1764 (2006).

Ewert, et al., Acute Left Heart Failure After Interventional Occlusion of An Artial Septal Defect, Z Kardiol, 90(5): 362-366 (May 2001).

Ewert, et al., Masked Left Ventricular Restriction in Elderly Patients With Atrial Septal Defects: A Contraindication for Closure?, Catheterization and Cardiovascular Intervention, 52:177-180 (2001).

Extended European Search Report dated Jan. 8, 2015 in EP Patent Appl No. 10772089.8.

Extended European Search Report dated Mar. 29, 2019 in EP Patent Appl. Serial No. EP16789391.

Extended European Search Report dated Sep. 19, 2006 in EP Patent Appl No. 16170281.6.

Feldman et al., "Transcatheter Interatrial Shunt Device for the Treatment of Heart Failure with Preserved Ejection Fraction (REDUCE LAP-HF I [Reduce Elevated Left Atrial Pressure in Patients With Heart Failure]), A Phase 2, Randomized, Sham-Controlled Trial," Circulation, 137:364-375 (2018).

Ferrari et al., "Impact of pulmonary arterial hypertension (PAH) on the lives of patients and carers: results from an international survey," Eur Respir J., 42:26312 (2013) (Abstract Only).

Fonarow et al., "Characteristics, Treatments, and Outcomes of Patients With Preserved Systolic Function Hospitalized for Heart Failure," J Am Coll Cardiol., 50(8):768-777 (2007).

Fonarow et al., "Risk Stratification for In-Hospital Mortality in Acutely Decompensated Heart Failure: Classification and Regression Tree Analysis," JAMA, 293(5):572-580 (2005).

Fonarow, G., "The Treatment Targets in Acute Decompensated Heart Failure," Rev Cardiovasc Med., 2:(2):S7-S12 (2001).

Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).

Galie et al., "Pulmonary arterial hypertension: from the kingdom of the near-dead to multiple clinical trial meta-analyses," Eur Heart J., 31:2080-2086 (2010).

Galipeau et al., "Surface acoustic wave microsensors and applications," Smart Materials and Structures, 6(6):658-667 (1997) (Abstract Only).

Geiran, et al., Changes in cardiac dynamics by opening an interventricular shunt in dogs, J. Surg. Res. 48(1): 6-12 (1990).

Gelernter-Yaniv, et al., Transcatheter ClosureoOf Left-To-Right Interatrial Shunts to Resolve Hypoxemia, Congenit. Heart Dis. 31(1): 47-53 (Jan. 2008).

Geva et al., "Atrial septal defects," Lancet, 383:1921-32 (2014).

Gewillig, et al., Creation with a stent of an unrestrictive lasting atrial communication, Cardio. Young 12(4): 404-407 (2002).

Gheorghiade et al., "Acute Heart Failure Syndromes, Current State and Framework for Future Research," Circulation, 112:3958-3968 (2005).

Gheorghiade et al., "Effects of Tolvaptan, a Vasopressin Antagonist, in Patients Hospitalized With Worsening Heart Failure A Randomized Controlled Trial," JAMA., 291:1963-1971 (2004).

Go et al. "Heart Disease and Stroke Statistics—2014 Update—A Report From the American Heart Association," Circulation, 128:1-267 (2014).

Guillevin et al., "Understanding the impact of pulmonary arterial hypertension on patients' and carers' lives," Eur Respir Rev., 22:535-542 (2013).

Guyton et al., "Effect of Elevated Left Atrial Pressure and Decreased Plasma Protein Concentration on the Development of Pulmonary Edema," Circulation Research, 7:643-657 (1959).

Hasenfub, et al., A Transcatheter Intracardiac Shunt Device for Heart Failure with Preserved Ejection Fraction (REDUCE LAP-HF): A Multicentre, Open-Label, Single-Arm, Phase 1 Trial, www.thelancet.com, 387:1298-1304 (2016).

Hoeper et al., "Definitions and Diagnosis of Pulmonary Hypertension," J Am Coll Cardiol., 62(5):D42-D50 (2013).

Hogg et al., "Heart Failure With Preserved Left Ventricular Systolic Function. Epidemiology, Clinical Characteristics, and Prognosis," J Am Coll Cardiol., 43(3):317-327 (2004).

Howell et al., "Congestive heart failure and outpatient risk of venous thromboembolism: A retrospective, case-control study," Journal of Clinical Epidemiology, 54:810-816 (2001).

Huang et al., "Remodeling of the chronic severely failing ischemic sheep heart after coronary microembolization: functional, energetic, structural, and cellular responses," Am J Physiol Heart Circ Physiol., 286:H2141-H2150 (2004).

Humbert et al., "Pulmonary Arterial Hypertension in France—Results from a National Registry," Am J Respir Crit Care Med., 173:1023-1030 (2006).

International Search Report & Written Opinion dated Nov. 7, 2016 in Int'l PCT Patent Appl. Serial No. PCT/IB2016/052561.

International Search Report & Written Opinion dated May 29, 2018 in Int'l PCT Patent Appl. Serial No. PCT/IB2018/051385.

International Search Report & Written Opinion dated Feb. 6, 2013 in Int'l PCT Patent Appl. No. PCT/IB2012/001859, 12 pages.

International Search Report & Written Opinion dated Feb. 7, 2020 in Int'l PCT Patent Appl. Serial No. PCT/IB2019/060257.

International Search Report & Written Opinion dated May 13, 2019 in Int'l PCT Patent Appl. No. PCT/IB2019/050452.

International Search Report & Written Opinion dated May 29, 2018 in Int'l PCT Patent Appl. Serial No. PCTIB2018/051355.

International Search Report & Written Opinion dated Jul. 20, 2020 in Int'l PCT Patent Appl. Serial No. PCT/IB2020/054699.

International Search Report & Written Opinion dated Aug. 28, 2012 in Int'l PCT Patent Appl. No. PCT/IL2011/000958.

International Search Report & Written Opinion dated Sep. 21, 2020 in Int'l PCT Patent Appl. Serial No. PCT/IB2020/054306.

International Search Report & Written Opinion dated Oct. 26, 2007 in Int'l PCT Patent Appl. Serial No. PCT/IB07/50234.

International Search Report dated Apr. 7, 2008 in Int'l PCT Patent Appl. Serial No. PCT/IL05/00131.

International Search Report dated Aug. 25, 2010 in Intl PCT Patent Appl. Serial No. PCT/IL2010/000354.

International Search Report dated Sep. 20, 2016 in Int'l PCT Patent Appl. Serial No. PCT/IB2016/052561.

ISR & Written Opinion dated Feb. 16, 2015 in Int'l PCT Patent Appl. Serial No. PCT/IB2014/001771).

Jessup et al. "2009Focused Update: ACC/AHA Guidelines for the Diagnosisand Management of Heart Failure in Adults: A Report of the American College ofCardiology Foundation/American Heart Association Task Force on PracticeGuidelines: Developed in Collaboration With the International Society for Heartand Lung Transplantation," J. Am. Coll. Cardiol., 53:1343-1382 (2009).

Jiang, G., "Design challenges of implantable pressure monitoring system," Frontiers in Neuroscience, 4(29):1-4 (2010).

Kane et al., "Integration of clinical and hemodynamic parameters in the prediction of long-term survival in patients with pulmonary arterial hypertension," Chest, 139(6):1285-1293 (2011) (Abstract Only).

(56) References Cited

OTHER PUBLICATIONS

Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:S67-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam-Webster OnLine Dictionary, Definition of "chamber", printed Dec. 20, 2004.
Mu et al., "Dual mode acoustic wave sensor for precise pressure reading," Applied Physics Letters, 105:113507-1-113507-5 (2014).
Nagaragu et al., "A 400μW Differential FBAR Sensor Interface IC with digital readout," IEEE., pp. 218-221 (2015).

Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-PRELIEVE Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial International Search dated Aug. 17, 2017 in Int'l PCT Patent Appl. Serial No. PCT/IB2017/053188.
Partial Supplemental European Search Report dated Dec. 11, 2018 in EP Patent Appl. Serial No. 16789391.6.
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin. 2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven., Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).

(56) References Cited

OTHER PUBLICATIONS

Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (REDUCE LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stormer, et al., Comparative Study of in Vitro Flow Characteristics Between a Human Aortic Valve and a Designed Aortic Valve and Six Corresponding Types of Prosthetic Heart Valves, European Surgical Research 8(2): 117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of DistributedSensor Networks, 14(11):1-8 (2018).
Supplementary European Search Report dated Nov. 13, 2009 in EP Patent Appl. Serial No. 05703174.2.
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131.
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Zhou, et al., Unidirectional Valve Patch for Repair of Cardiac Septal Defects with Pulmonary Hypertension, Annals of Thoracic Surgeons, 60:1245-1249, (1995).

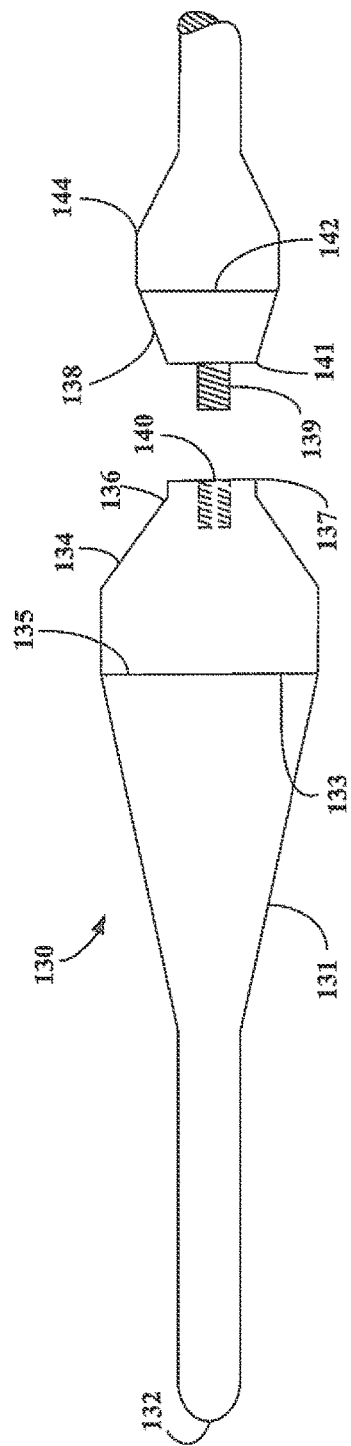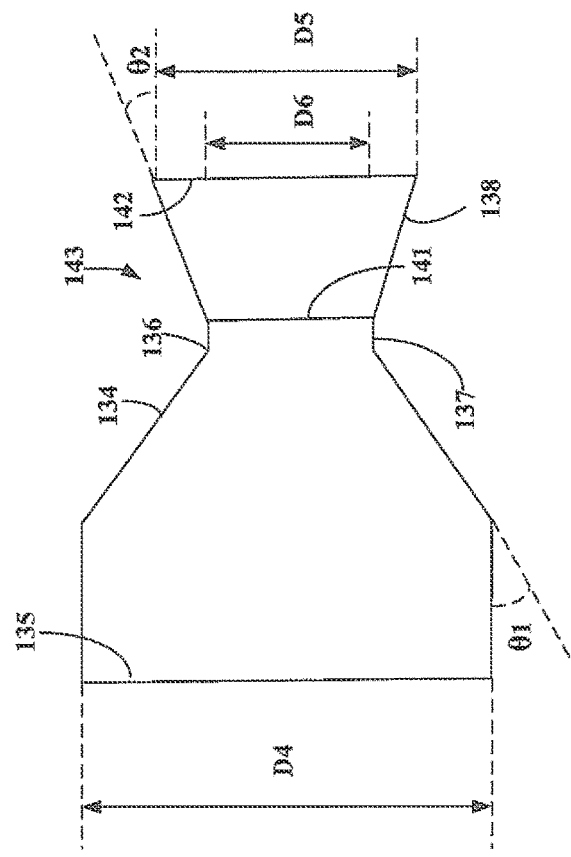
FIG. 3
FIG. 4

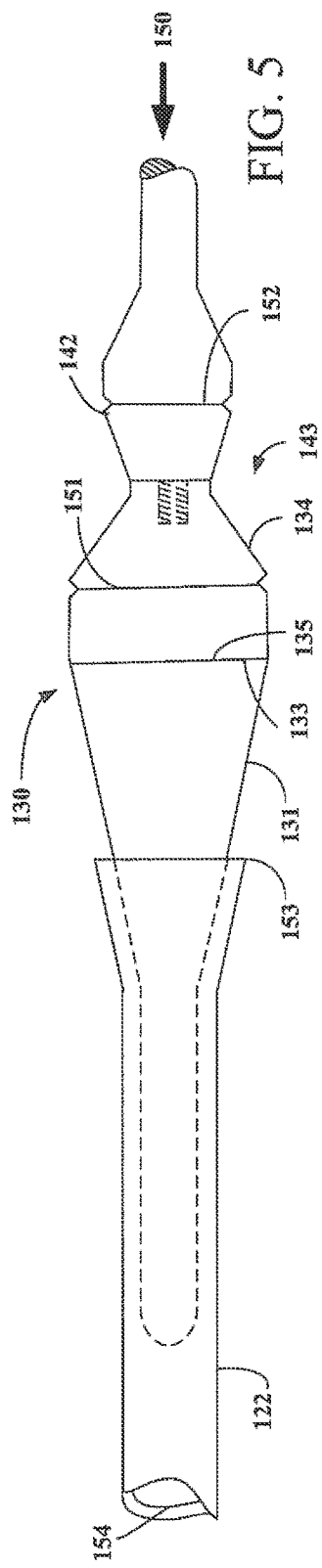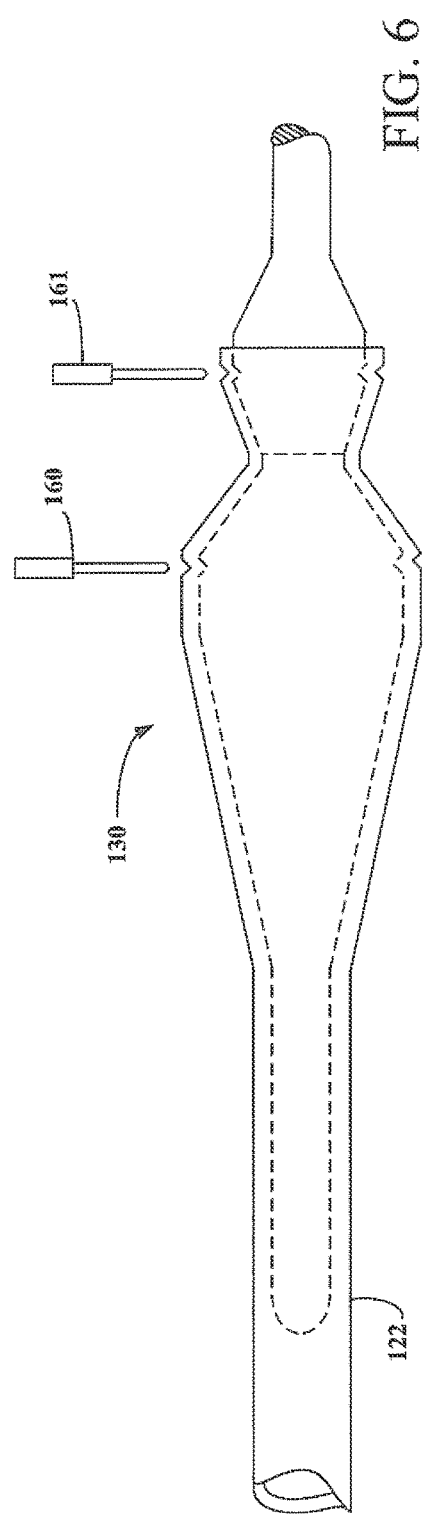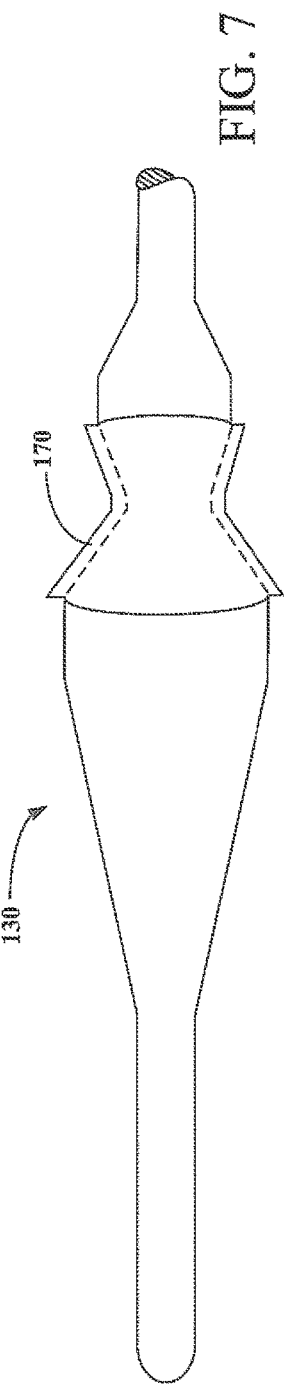

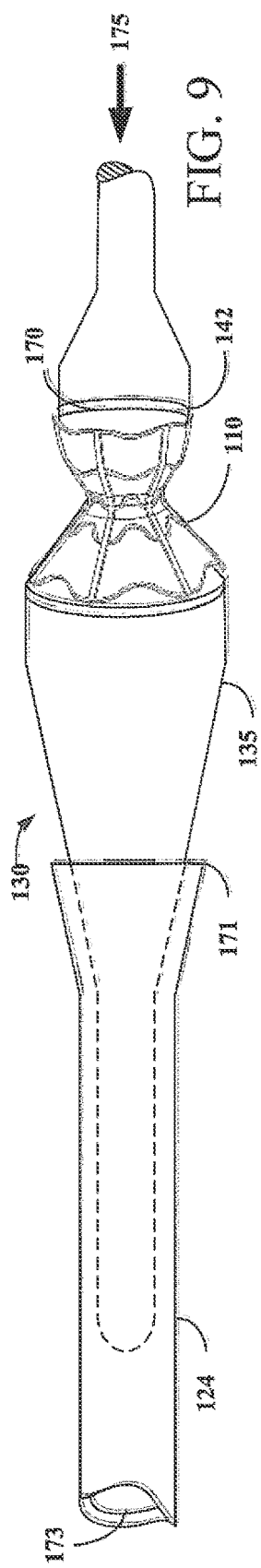
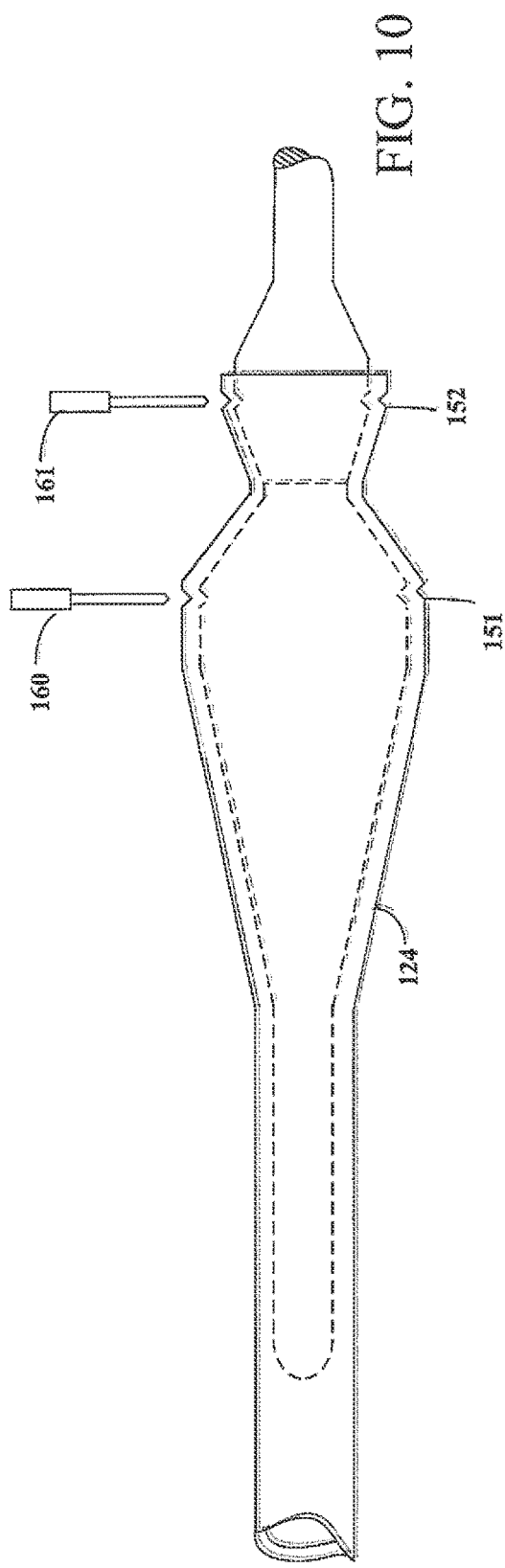
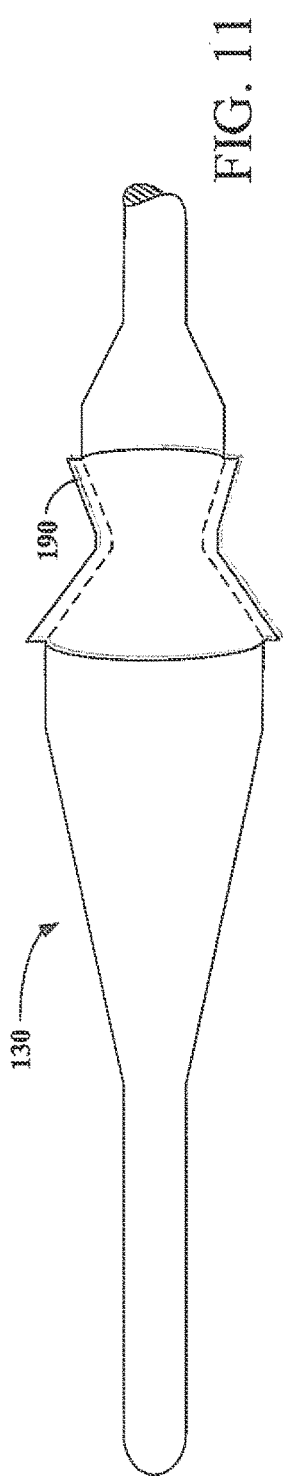

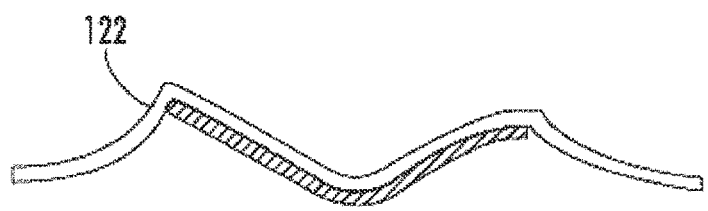
FIG. 14A
FIG. 14B
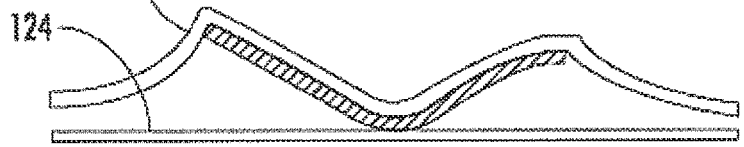
FIG. 14C
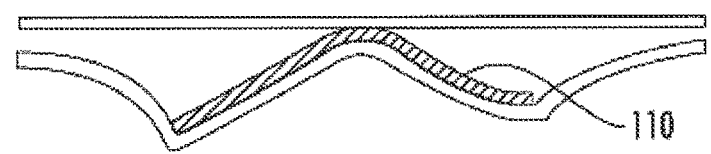
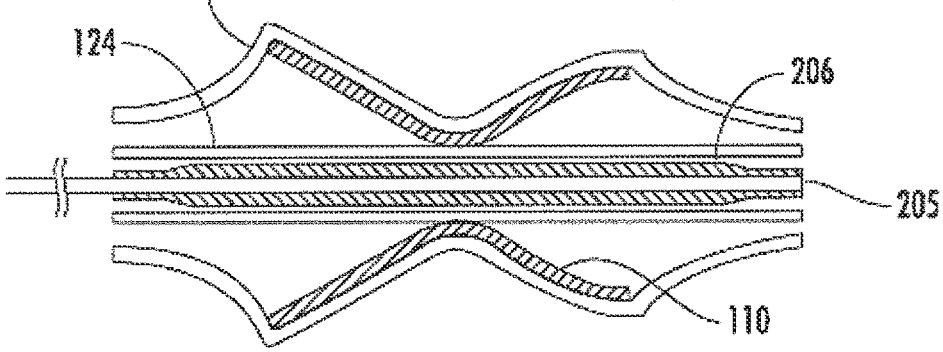
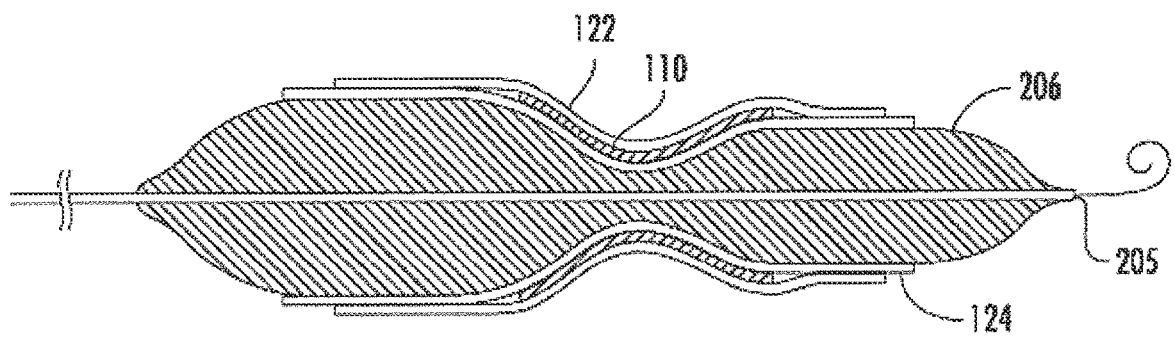
FIG. 14D

SYSTEMS AND METHODS FOR MAKING ENCAPSULATED HOURGLASS SHAPED STENTS

CROSS-REFERENCE TO RELATED APPLICATIONS

This application is a divisional of U.S. patent application Ser. No. 16/205,213, filed Nov. 29, 2018, now U.S. Pat. No. 10,835,394, which is a continuation-in-part of U.S. patent application Ser. No. 15/798,250, filed Oct. 30, 2017, which is a continuation application of U.S. patent application Ser. No. 15/608,948, filed May 30, 2017, published as U.S. Patent Application Pub. No. 2017/0340460, which claims priority to U.S. Provisional Patent Application Ser. No. 62/343,658, filed May 31, 2016, the entire contents of each of which are incorporated by reference herein.

This application is also a continuation of PCT International Patent Application Serial No. PCT/IB2019/060257, filed Nov. 27, 2019, which claims priority to U.S. patent application Ser. No. 16/205,213, filed Nov. 29, 2018, now U.S. Pat. No. 10,835,394, the entire contents of each of which are incorporated by reference herein.

FIELD OF THE INVENTION

This application relates to systems and methods for the manufacture of encapsulated stents for treating congestive heart failure and other disorders treated with encapsulated stents.

BACKGROUND

Heart failure is the physiological state in which cardiac output is insufficient to meet the needs of the body and the lungs. Congestive Heart Failure (CHF) occurs when cardiac output is relatively low due to reduced contractility or heart muscle thickening or stiffness. There are many possible underlying causes of CHF, including myocardial infarction, coronary artery disease, valvular disease, and myocarditis.

CHF is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the hearts contractions become weakened, and the heart failure worsens. Another compensatory mechanism is vasoconstriction of the arterial system. This mechanism, like salt and water retention, raises the blood pressure to help maintain adequate perfusion.

In low ejection fraction (EF) heart failure, high pressures in the heart result from the body's attempt to maintain the high pressures needed for adequate peripheral perfusion. However, the heart weakens as a result of the high pressures, aggravating the disorder. Pressure in the left atrium may exceed 25 mmHg, at which stage, fluids from the blood flowing through the pulmonary circulatory system flow out of the interstitial spaces and into the alveoli, causing pulmonary edema and lung congestion.

CHF is generally classified as either Heart Failure with reduced Ejection Fraction (HFrEF) or Heart Failure with preserved Ejection Fraction (HFpEF). In HFrEF, the pumping action of the heart is reduced or weakened. A common clinical measurement is the ejection fraction, which is a function of the blood ejected out of the left ventricle (stroke volume), divided by the maximum volume remaining in the left ventricle at the end of diastole or relaxation phase (End Diastolic Volume). A normal ejection fraction is greater than 50%. HFrEF has a decreased ejection fraction of less than 40%. A patient with HFrEF may usually have a larger left ventricle because of a phenomenon called cardiac remodeling that occurs secondarily to the higher ventricular pressures.

In HFpEF, the heart generally contracts normally, with a normal ejection fraction, but is stiffer, or less compliant, than a healthy heart would be when relaxing and filling with blood. This stiffness may impede blood from filling the heart, and produce backup into the lungs, which may result in pulmonary venous hypertension and lung edema. HFpEF is more common in patients older than 75 years, especially in women with high blood pressure.

Both variants of CHF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. However, pharmacological approaches are not always successful, as some people may be resistant or experience significant side effects In more severe cases of CHF, assist devices such as mechanical pumps have been used to reduce the load on the heart by performing all or part of the pumping function normally done by the heart. Chronic left ventricular assist devices (LVAD), and cardiac transplantation, often are used as measures of last resort. However, such assist devices are typically intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and the risk of hemolysis, thrombus formation, and infection. In addition to assist devices, surgical approaches such as dynamic cardiomyoplasty or the Batista partial left ventriculectomy may also be used in severe cases. However these approaches are highly invasive and have the general risks associated with highly invasive surgical procedures.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome (HLHS). Amplatz describes that increasing mixing of pulmonary and systemic venous blood improves oxygen saturation. Amplatz describes that depending on the hemodynamics, the shunting passage can later be closed by an occluding device. However, Amplatz is silent on the treatment of CHF or the reduction of left atrial pressure, and is also silent on means for regulating the rate of blood flow through the device.

U.S. Pat. No. 8,070,708 to Rottenberg describes a method and device for controlling in-vivo pressure in the body, and in particular, the heart. The device described in Rottenberg involves a shunt to be positioned between two or more lumens in the body to permit fluid to flow between the two lumens. The Rottenberg patent further describes that an adjustable regulation mechanism may be configured to cover an opening of the shunt to regulate flow between the two lumens. The shunt is configured such that the flow permitted is related to a pressure difference between the two lumens. The adjustable regulation mechanism may be remotely activated. The Rottenberg patent describes that the device described may be used to treat CHF by controlling pressure difference between the left atrium and the right atrium. While Rottenberg describes a mechanism for treating CHF by controlling the flow between the left atrium and the right atrium, it does not describe the encapsulation of an hourglass shaped stent.

U.S. Patent Publication No. 2005/0165344 to Dobak, III describes an apparatus for treating heart failure that includes a conduit positioned in a hole in the atrial septum of the heart, to allow flow from the left atrium into the right atrium. Dobak describes that the shunting of blood will reduce left atrial pressures, thereby preventing pulmonary edema and progressive left ventricular dysfunction, and reducing LVEDP. Dobak describes that the conduit may include a self-expandable tube with retention struts, such as metallic arms that exert a slight force on the atrial septum on both sides and pinch or clamp the valve to the septum, and a one-way valve member, such as a tilting disk, bileaflet design, or a flap valve formed of fixed animal pericardial tissue. However, Dobak states that a valved design may not be optimal due to a risk of blood stasis and thrombus formation on the valve, and that valves can also damage blood components due to turbulent flow effects. Dobak does not provide any specific guidance on how to avoid such problems.

U.S. Pat. No. 9,034,034 to Nitzan, incorporated herein by reference, describes a device for regulating blood pressure between a patient's left atrium and right atrium which comprises an hourglass-shaped stent having a neck region and first and second flared regions, the neck region disposed between the first and second end regions and configured to engage the fossa ovalis of the patient's atrial septum. Nitzan describes that the hourglass shaped stent is also encapsulated with a biocompatible material. While Nitzan describes a method for the manufacture of an hourglass shaped stent for the treatment of CHF, Nitzan is silent on the method of encapsulating the stent.

U.S. Pat. No. 6,214,039 to Banas, incorporated herein by reference, describes a method for covering a radially endoluminal stent. In the method described by Banas, the encapsulated stent is assembled by joining a dilation mandrel and a stent mandrel, placing the graft on the dilation mandrel where it is radially expanded, and passing the expanded graft over the stent that is positioned on the stent mandrel. While Banas describes a method for encapsulating a cylindrical stent, the method in Banas does not describe encapsulation of an hourglass shaped stent intended for treatment of CHF. The method for assembling the covered stent and mandrel assembly described in Banas would be inappropriate for assembly of an hourglass stent described in Nitzan.

U.S. Pat. No. 6,797,217 to McCrea, incorporated herein by reference, describes a method for encapsulating stent-grafts. McCrea describes methods for encapsulating an endoluminal stent fabricated from a shape memory alloy. The Method described by McCrea involves an endoluminal stent encapsulated in an ePTFE covering which circumferentially covers both the luminal and abluminal walls along at least a portion of the longitudinal extent of the endoluminal stent. McCrea further describes applying pressure to the stent-graft assembly and heating the assembly to complete the encapsulation. While McCrea describes an encapsulated endoluminal stent, it does not describe the encapsulation of an hourglass shaped stent for the treatment of CHF.

In view of the above-noted drawbacks of previously known systems, it would be desirable to provide systems and methods of manufacture of encapsulated hourglass shaped stents for treating congestive heart failure and other disorders treated with hourglass shaped stent-graft assemblies.

SUMMARY OF THE INVENTION

The present invention overcomes the drawbacks of previously-known systems and methods by providing systems and methods for making encapsulated hourglass shaped stents for treating CHF and other conditions benefited by encapsulated hourglass shaped stents such as pulmonary hypertension. The hourglass or "diabolo" shaped stents are configured to be encapsulated using a mandrel assembly.

In accordance with one aspect, a method for making an encapsulated stent-graft may involve, providing a mandrel having a first conical region with a first apex and a second conical region with a second apex, placing an expandable stent having an hourglass shape in an expanded form on the mandrel so that a first flared region of the expandable stent conforms to the first conical region and a second flared region of the expandable stent conforms to the second conical region, associating a biocompatible material with the expandable stent to form a stent-graft assembly, and compressing the stent-graft assembly against the mandrel to form the encapsulated stent-graft. The first conical region and the second conical region may be aligned so that the first and second apexes contact one another.

The biocompatible material may have first and second ends and associating the biocompatible material with the expandable stent involves placing the biocompatible material within a lumen of the expandable stent. The method may further include placing a second biocompatible material over the expandable stent. Compressing the stent-graft assembly may involve winding a layer of tape over the biocompatible material to compress the stent-graft assembly against the mandrel. The expandable stent may include through-wall openings, and the method may further involve heating the stent-graft assembly to cause the biocompatible material and the second biocompatible material to bond to one another through the through-wall openings. Heating the stent-graft assembly may cause the biocompatible material and the second biocompatible material to become sintered together to form a monolithic layer of biocompatible material. The method may further involve applying a layer of Fluorinated Ethylene Propylene (FEP) to biocompatible material or second biocompatible material. The biocompatible material may be pre-formed. The method may further involve manipulating the encapsulated stent-graft to a compressed shape and loading the encapsulated stent-graft into a delivery sheath. A first end diameter of the expandable stent may be different in size from a second end diameter. The mandrel may have a neck region disposed between a first conical region and a second conical region and the mandrel may be configured to be removably uncoupled at the neck region into a first half having at least the first conical region and a second half having at least the second conical region.

In accordance with another aspect, a method for making an encapsulated stent-graft may involve providing a mandrel assembly having an asymmetric shape, providing an expandable stent in an expanded form, coupling a biocompatible material to the expandable stent to form a stent-graft assembly, and compressing the stent-graft assembly on the mandrel assembly to form the encapsulated stent-graft. The expandable stent may be configured to conform to the asymmetric shape formed by the mandrel assembly.

The expandable stent and the biocompatible material may be coupled on the mandrel assembly or before placement on the mandrel assembly. The method may further involve coupling a second biocompatible material to an opposing surface of the expandable stent to form the stent-graft assembly. The second biocompatible material may be formed of a same or different material as the biocompatible material. The mandrel assembly may include a first mandrel and a second mandrel, and the method may further involve, positioning the first mandrel within the first end of the expandable stent such that a portion of the second biocompatible material is positioned between the first mandrel and the expandable stent, and positioning the second mandrel within the second end of the expandable stent such that a portion of the second biocompatible material is positioned between the second mandrel and the expandable stent. The biocompatible material may be a pre-formed biocompatible graft layer having the shape of the expandable stent. The pre-formed biocompatible graft layer may engage the expandable stent on the mandrel assembly.

In accordance with yet another aspect, a method for making an encapsulated stent-graft may involve providing an asymmetrical stent, placing a first biocompatible material over the asymmetrical stent, providing a second biocompatible material for placement within the asymmetrical stent, inserting a balloon catheter having an inflatable balloon within the asymmetrical stent in a deflated state such that the second biocompatible material is between the asymmetrical stent and the inflatable balloon, and inflating the inflatable balloon to an inflated state conforming to the shape of the asymmetrical stent, thereby causing the second biocompatible material to engage with the asymmetrical stent to form the encapsulated stent-graft.

The method may further involve controlling the pressure within the balloon to achieve a desired adhesion between the first biocompatible material and the second biocompatible material. The method may further involve controlling the pressure within the balloon to achieve a desired inter-nodal-distance of the graft material. The second biocompatible material may be placed within the asymmetrical stent prior to inserting the balloon catheter within the asymmetrical stent. The second biocompatible material may be disposed on the inflatable balloon, and inflating the inflatable balloon may cause the second biocompatible material disposed on the inflatable balloon to contact and inner surface of the asymmetrical stent thereby engaging the second biocompatible material with the asymmetrical stent.

In accordance with yet another aspect, a method for making an encapsulated stent-graft may involve providing a funnel having a large end and a small end, placing an asymmetric stent with a first end, a second end, an exterior surface and an interior surface within the large end of the funnel, placing a biocompatible tube over the small end of the funnel, the biocompatible tube having a stent receiving portion and a remaining portion, advancing the asymmetric stent through the funnel and out the small end of the funnel, thereby depositing the asymmetric stent into the biocompatible tube such that the stent is positioned within the stent receiving portion of the biocompatible tube, thereby engaging an exterior surface of the asymmetric stent with the biocompatible tube, pulling the remaining portion of the biocompatible tube through the first end of the asymmetric stent and out the second end, introducing a first mandrel having a shape similar to the first side of the asymmetric stent into the first side of asymmetric stent thereby engaging the interior surface of the first side of the asymmetric stent with a portion of the remaining portion of the biocompatible tube, and introducing a second mandrel having a shape similar to the second side of the asymmetric stent into the second side of the asymmetric stent thereby engaging the interior surface of the second side of the asymmetric stent with a portion of the remaining portion of the biocompatible tube.

In accordance with yet another aspect, an hourglass shaped mandrel assembly for making an encapsulated stent-graft may involve a first portion having at least a first conical region having a flared end with a first diameter and an apex end with a second diameter, a second portion having at least a second conical region having a flared end with third diameter and an apex end with a fourth diameter, and a tapered region coupled to the flared end of the first portion and extending away from the flared end of the first portion. The tapered region may have a flared end with a fifth diameter and a tapered end with a sixth diameter such that the fifth diameter is equal to the first diameter and the sixth diameter is smaller than the fifth diameter. The first conical region of the first portion and the second conical region of the second portion may be aligned so that apexes of the first portion and second portion are contacting one another. The hourglass shaped mandrel assembly may further include a neck region positioned between the apex end of the first portion and the apex end of the second portion such that the neck region is affixed to at least the first portion or the second portion. The first portion and the second portion may be removably coupled at the apex end of the first portion and the apex end of the second portion. The hourglass shaped mandrel may be configured to expand radially.

In accordance with yet another aspect, a method for making an encapsulated stent-graft may involve providing a stent having a first flared region, a second flared region and a neck region therebetween. The stent may be compressed and the second flared region and neck region may be placed within a graft tube and permitted to expand depositing a first portion of graft tube on the second flared region and neck region. The graft tube may be guided through the interior of the stent such that it extends beyond the first flared region, depositing a second portion of graft material upon the interior of the stent. A first mandrel portion having a similar shape as the first flared portion but with slightly smaller dimensions may be placed within the first flared region while simultaneously positioning the second end of the graft tube over the first mandrel portion. A second mandrel portion having a similar shape as the second flared region but with slightly smaller dimensions may be placed within the second flared region. A second end of the graft tube may be separated from the first mandrel portion and positioned over the first flared region and neck region to deposit a third portion of graft tube over the first flared region and neck region of the stent, resulting a stent-graft assembly. A flexible sleeve having a similar size and shape to the stent-graft assembly and a longitudinal opening may be positioned around the stent-graft assembly. A compressor having two halves and an indentation having a similar size and shape as the flexible sleeve covering the stent-graft assembly may be coupled to the flexible sleeve to compresses the stent-graft assembly against the mandrel. Heat may be applied to the resulting assembly to create monolithic layer of biocompatible material and ultimately generate an encapsulated stent.

In accordance with yet another aspect, a stent-graft assembly may involve an expandable stent having an exterior, a lumen and a first length that includes a first region and first end, a second region and a second end, and a middle region positioned between the first region and the second region. The stent-graft assembly may further involve a biocompatible graft-tube having a second length greater than twice the first length of the stent. The second length of the biocompatible graft-tube may have first, second, and third portions. The first portion may extend through the lumen from the first end of the first region, through the middle region and to the second end of the second region. The second portion may be continuously joined to the first portion at the first end and extend along the exterior of the stent from the first end and into the middle region. The third portion may be continuously joined to the second portion at the second end and extend along the exterior of the second region and into the middle region. In this manner, the second and third portions may overlap and may be joined to one another in the middle region.

In accordance with yet another aspect, a method for making an encapsulated stent-graft may involve compressing a stent having a first flared region, a second flared region, and a neck region situated between the first flared region and the second flared region, into a compressed state. The method may further involve positioning the second flared region and the neck region within a graft tube having a first end and a second end, thereby depositing a first layer of graft material over the neck region and the second flared region. Additionally, the second end of the graft tube may be guided into the second flared region, through an interior portion of the stent, and out the first flared region, thereby depositing a second layer of graft material along the interior portion of the stent. After guiding the second end of the graft tube out the first flared region, the second end of the graft tube may be guided over the first flared region and over the neck region, thereby depositing a third layer of graft material over the first flared region and the neck region. The stent and graft tube may form a stent-graft assembly. It is understood that guiding the second end of the graft tube into the second flared region, through an interior portion of the stent, and out the first flared region may include everting the second end of the graft tube, and guiding the second end of the graft tube over the first flared region and over the neck region may include everting the second end of the graft tube.

Depositing a first layer of graft material may further involve expanding at least the second flared region to an expanded state within the first end of the graft tube. Additionally, the method may further involve expanding the first flared region after releasing the second flared region. At least one additional layer of graft material may be seamlessly deposited over at least a portion of the stent using the graft tube. The first flared region may have a maximum diameter that is larger than a maximum diameter of the second flared region and the second flared region may have a diameter that is larger than the neck region.

The method may further involve selecting a mandrel involving a first portion having a first mandrel end that is removably coupled to a second portion having a second mandrel end, and guiding the first flared region onto the first portion of the mandrel while guiding the second end of the graft tube over the first portion of the mandrel such that the second end of the graft tube extends beyond the first flared region. The method may further involve coupling the second mandrel end of the second portion of the mandrel to the first mandrel end of the first portion of the mandrel. The method may further involve selecting a flexible sleeve having a first sleeve end and a second sleeve end and a shape configured to receive the stent-graft assembly, flexing the flexible sleeve such that the first sleeve end is separated from the second sleeve end, and positioning the flexible sleeve over the stent-graft assembly while the stent-graft assembly is positioned on the mandrel. Selecting the flexible sleeve may involve selecting a flexible sleeve comprised of silicone, having wall thickness that is constant, having a varying thickness, or selecting a flexible sleeve sized and configured to reduce an inter nodal distance within the graft tube.

The method may further involve selecting a compressor involving a first half that is removably coupled to a second half, the first half and the second half each involving an interior surface having an indentation sized and configured to receive the flexible sleeve covering the stent-graft assembly, positioning the first half and the second half of the compressor around the flexible sleeve covering the stent-graft assembly, and coupling the first half of the compressor to the second half of the compressor while the first half of the compressor and the second half of the compressor are positioned around the flexible sleeve covering the stent-graft assembly, wherein the compressor, the flexible sleeve, the stent-graft assembly, and the mandrel form a sintering assembly. Selecting a compressor may involve selecting a compressor comprised of stainless steel, selecting a compressor having a thickness that facilities heat-transfer to the stent-graft assembly, selecting a compressor that applies a uniform compression force to the stent-graft assembly, selecting a compressor that applies a compression force to stent-graft assembly that varies, or selecting a compressor sized and configured to reduce an inter nodal distance within the graft tube.

Coupling the first half of the compressor to the second half of the compressor may involve applying a compression force to the flexible sleeve, thereby compressing the stent-graft assembly against the mandrel. The flexible sleeve may facilitate even distribution of the compression force applied to the stent-graft assembly by the compressor. The method may further involve heating the sintering assembly to cause the first layer, the second layer, and the third layer of graft material to become sintered together to form a monolithic layer of graft material, thereby forming the encapsulated stent-graft. The stent may involve through-wall openings and heating the sintering assembly may cause the three layers and two layers of graft material to bond to one another through the through-wall openings. The flexible sleeve may be silicone and heating the sintering assembly may cause the flexible sleeve to deposit silicone fragments into the stent-graft assembly. The method may further involve winding a layer of tape over the flexible sleeve to compress the stent-graft assembly against the mandrel.

In accordance with yet another aspect, a stent-graft assembly may involve an expandable stent involving a first flared region, a neck region, and a second flared region, the neck region positioned between the first flared region and the second flared region. The stent-graft assembly may further involve a continuous biocompatible graft-tube covering the expandable stent, the continuous biocompatible graft tube involving a first end and a second end, and first, second, and third portions, the first end of the biocompatible graft tube being an end of the first graft portion and the second end of the biocompatible graft tube being an end of the third graft portion, the first graft portion deposited on the neck region and the second flared region of the expandable stent, the second graft portion deposited along an interior surface of the expandable stent and adjacent to the first graft portion and the third graft portion, and the third graft portion deposited along the first flared region and the neck region of the expandable stent, such that the first flared region is covered by two layers of biocompatible material involving the second graft portion and the third graft portion, the neck region is covered by three layers of biocompatible material involving the first graft portion, the second graft portion, and the third graft portion, and the second flared region is covered by two layers of biocompatible material involving the second graft portion and the first graft portion.

The first, second, and third portions of biocompatible graft tube may become sintered together into a monolithic layer of graft material upon application of heat, thereby forming an encapsulated stent-graft. The expandable stent may involve through-wall openings such that the application of heat causes the first, second, and third portions to bond to one another through the through-wall openings. The encapsulated stent-graft may be configured to transition from a compressed state to an expanded state. The expandable stent may be formed from NITINOL and may be configured to transition the encapsulated stent-graft from the compressed state to the expanded state. The encapsulated stent-graft may be configured to transition from the compressed state to the expanded state using an inflatable balloon.

In accordance with yet another aspect, a stent-graft assembly may involve an expandable stent having an exterior, a lumen and a first length that includes a first region and first end, a second region and a second end, and a middle region positioned between the first region and the second region, and a biocompatible graft-tube having a second length greater than twice the first length, the second length having first, second, and third portions, wherein the first portion extends through the lumen from the first end of the first region, through the middle region and to the second end of the second region, the second portion is continuously joined to the first portion at the first end and extends along the exterior from the first end and into the middle region, and the third portion is continuously joined to the second portion at the second end and extends along the exterior of the second region and into the middle region, such that the second and third portions overlap and are joined to one another in the middle region.

The first, second and third portions of biocompatible graft tube may be sintered together upon application of heat. The expandable stent may involve through-wall openings such that the first, second, and third portions bond to one another through the through-wall openings upon application of heat to form an encapsulated stent-graft. The encapsulated stent-graft may be configured to transition from a compressed state to an expanded state. The expandable stent may be formed from NITINOL and may be configured to transition the encapsulated stent-graft from the compressed state to the expanded state. The encapsulated stent-graft is configured to transition from the compressed state to the expanded state using an inflatable balloon. At least one of the first region and the second region may flare outwardly at the first end or second end, respectively.

BRIEF DESCRIPTION OF THE DRAWINGS

FIG. 3 is a partially exploded side view of assembly apparatus for manufacturing hourglass stent-graft assembly in accordance with the methods of the present invention.

FIG. 4 is a side view of hourglass shaped mandrel assembly section of assembly apparatus for manufacturing hourglass shaped stent-graft assembly in accordance with the methods of the present invention.

FIG. 5 is a side view of assembly apparatus engaged with first graft tube at the tapered region.

FIG. 6 is a side view of assembly apparatus engaged with first graft tube over hourglass shaped mandrel assembly section.

FIG. 7 is a side view of first graft layer disposed over hourglass shaped mandrel assembly section of assembly apparatus.

FIG. 9 is a side view of assembly apparatus engaged with second graft tube at the tapered region.

FIG. 10 is a side view of assembly apparatus engaged with second graft tube over hourglass shaped mandrel assembly section of assembly apparatus.

FIG. 11 is a side view of stent-graft disposed over hourglass shaped mandrel assembly section.

FIGS. 14A-14D are side views sequentially illustrating an encapsulation technique involving an inflatable balloon.

DETAILED DESCRIPTION

Embodiments of the present invention are directed to systems and methods for the manufacture of hourglass or "diabolo" shaped stents encapsulated with biocompatible material for treating subjects suffering from congestive heart failure (CHF) or alternatively pulmonary hypertension. The hourglass or "diabolo" shaped stents are configured to be encapsulated using an hourglass shaped mandrel assembly having a dilation portion and two conical regions that may be removably coupled. The hourglass shaped stents may be specifically configured to be lodged securely in the atrial septum, preferably the fossa ovalis, to allow blood flow from the left atrium to the right when blood pressure in the left atrium exceeds that on the right atrium. The resulting encapsulated stents are particularly useful for the purpose of inter-atrial shunting as they provide long-term patency and prevent tissue ingrowth within the lumen of the encapsulated stent. However, it is understood that the systems and methods described herein may also be applicable to other conditions benefited from an encapsulated hourglass shaped stent such as pulmonary hypertension wherein the encapsulated hourglass shaped stent is used as a right-to-left shunt.

Figure 1:
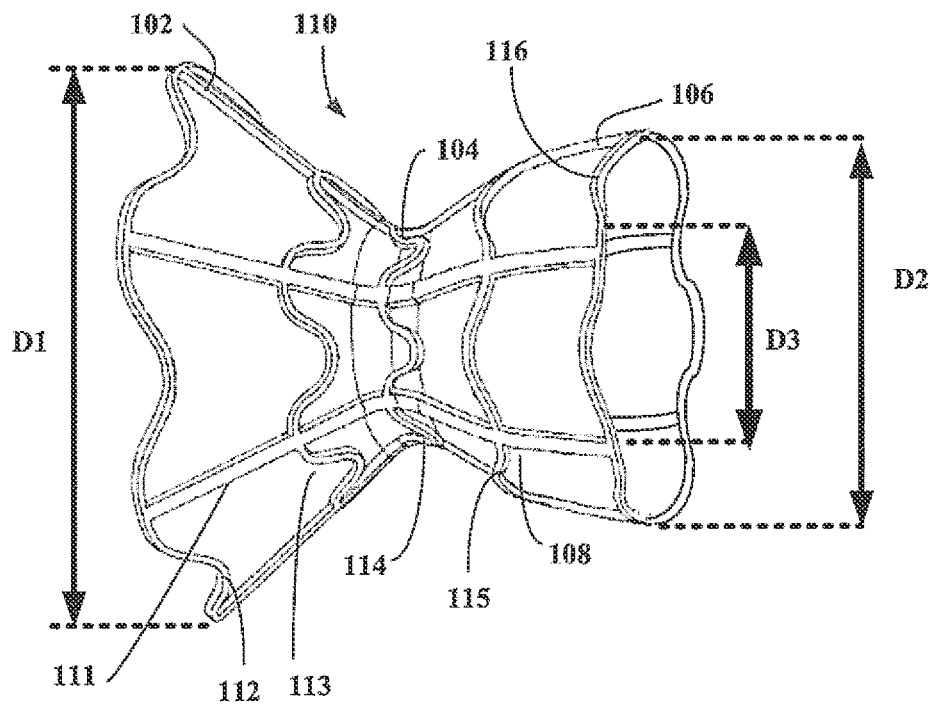
FIG. 1 is side view of hourglass shaped stent constructed in accordance with the methods of the present invention.

Referring now to FIG. 1, stent 110 is illustrated. Stent 110 is hourglass or "diabolo" shaped and may be radially expandable to an expanded state and/or compressible to a compressed state. Stent 110 may be self-expandable or may be manually expandable. For example, stent 110 may be transitioned from a compressed state to an expanded state using a balloon expandable. Stent 110 has three general regions: first flared region 102, second flared region 106, and neck region 104 disposed between the first and second flared regions. First flared region 102 has first end region diameter D1, second flared region 106 has second end region diameter D2, and neck region 104 has neck diameter D3. As shown in FIG. 1, neck region 104 of stent 110 is significantly narrower than first flared region 102 and second flared region 106. Also shown in FIG. 1, stent 110 may be asymmetric. For example, first flared region 102 may have a maximum diameter that is larger than a maximum diameter of second flared region 106. Stent 110 may be asymmetric to take advantage of the natural features of the atrial septum of the heart as well as the left and right atrium cavities. Alternatively, hourglass shaped stent 110 may be symmetric with the first end region diameter D1 being equal to the second end region diameter D2. First flared region 102 and second flared region 106 also may have either straight or curved profiles or both. For example, strut 111 has a straight profile and strut 108 has a curved profile. Additionally, first flared region 102 and second flared region 106 may assume any angular position consistent with the hour-glass configuration.

Stent 110 is preferably comprised of a self-expanding material having superelastic properties. For example, a shape-memory metal such as nickel titanium (NiTi), also known as NITINOL may be used. Other suitable materials known in the art of deformable stents for percutaneous implantation may alternatively be used such as other shape memory alloys, self-expanding materials, superelastic materials, polymers, and the like. The tube may be laser-cut to define a plurality of struts and connecting members. For example, as illustrated in FIG. 1, the tube may be laser-cut to define a plurality of sinusoidal rings connected by longitudinally extending struts. Struts 108 and 111 and sinusoidal rings 112-116 illustrated in FIG. 1 may be laser cut to form an integral piece of unitary construction. Alternatively, struts 111 and sinusoidal rings 112-116 may be separately defined to form different pieces of shape-memory metal and subsequently coupled together to form stent 110. The stent may also be electropolished to reduce thrombogenicity.

Stent 110 may be expanded on a mandrel to define first flared region 102, second flared region 106, and neck region 104. The expanded stent then may be heated to set the shape of stent 110. The stent may be expanded on a mandrel in accordance with the teachings of U.S. Pat. No. 9,034,034 to Nitzan and may take the form of a stent described in that patent, U.S. Pat. No. 9,707,382 to Nitzan, and/or U.S. Pat. No. 10,076,403 to Eigler, the entire contents of each of which are incorporated by reference herein. In one example, stent 110 is formed from a tube of NITINOL, shaped using a shape mandrel, and placed into an oven for 11 minutes at 530° C. to set the shape. The mandrel disclosed in FIGS. 3-4 may be configured as a shaping mandrel to set the shape of stent 110 or, alternatively, a different mandrel may be used as the shaping mandrel.

Figure 2:
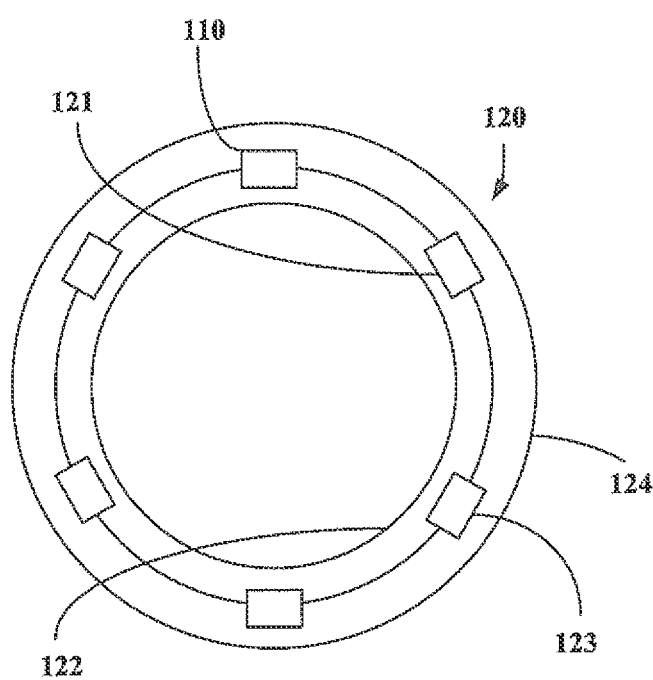
FIG. 2 is a cross-section view of hourglass shaped stent encapsulated with first and second graft layers.

Referring now to FIG. 2, stent 110 is at least partially covered with biocompatible material, as shown in FIG. 2, to create stent-graft assembly 120. Biocompatible material may be expanded polytetrafluoroethylene (ePTFE), silicone, polycarbonate urethane, DACRON (polyethylene terephthalate), Ultra High Molecular Weight Polyethylene (UHMWPE), or polyurethane, or of a natural material such as pericardial tissue, e.g., from an equine, bovine, or porcine source or human tissue such as human placenta or other human tissues. The biocompatible material is preferably smooth so as to inhibit thrombus formation, and optionally may be impregnated with carbon so as to promote tissue ingrowth. Alternatively, to promote tissue ingrowth and endothelization, the biocompatible material may form a mesh-like structure. The biocompatible material may be pre-shaped using a dedicated pre-shaping mandrel and heat treatment to simplify the mounting of the biocompatible material on an encapsulation mandrel, as discussed in detail below. Pre-shaping the biocompatible material has been shown to simplify the handling and mounting of the biocompatible material on the mandrel, thereby reducing stretching and the risk for tears in the biocompatible material and may be especially beneficial for encapsulating asymmetrical stents. Portions of stent 110 such as first flared region 102 may not be covered with the biocompatible material.

Generally, the stent is positioned between a first and second layer of graft material by covering inner surface 121 of stent 110 with first graft layer 170, and covering outer surface 123 of stent 110 with second graft layer 190. First graft layer 170 and second graft layer 190 each may have a first end and a second end and may have lengths that are about equal. Alternatively, first graft layer 170 and second graft layer 190 may have different lengths. Stent 110 may have a length that is shorter than the length of first graft layer 170 and second graft layer 190. In other embodiments, stent 110 may have a length that is longer than the length of first graft layer 170 and/or second graft layer 190. As discussed in detail below, two or more graft layers may cover the stent or portions of the stent. As also discussed below, the graft layers may be securely bonded together to form a monolithic layer of biocompatible material. For example, first and second graft tubes may be sintered together to form a strong, smooth, substantially continuous coating that covers the inner and outer surfaces of the stent. Portions of the coating then may be removed as desired from selected portions of the stent using laser-cutting or mechanical cutting, for example.

In a preferred embodiment, stent 110 is encapsulated with ePTFE. It will be understood by those skilled in the art that ePTFE materials have a characteristic microstructure consisting of nodes and fibrils, with the fibrils orientation being substantially parallel to the axis of longitudinal expansion. Expanded polytetrafluoroethylene materials are made by ram extruding a compressed billet of particulate polytetrafluoroethylene and extrusion lubricant through an extrusion die to form sheet or tubular extrudates. The extrudate is then longitudinally expanded to form the node-fibril microstructure and heated to a temperature at or above the crystalline melt point of polytetrafluoroethylene, i.e., 327° C., for a period of time sufficient to sinter the ePTFE material. Heating may take place in a vacuum chamber to prevent oxidation of the stent. Alternatively, heating may take place in a nitrogen rich environment. A furnace may be used to heat the stent-graft assembly. Alternatively, or in addition to, the mandrel upon which the stent-graft assembly rests may be a heat source used to heat the stent-graft assembly.

FIGS. 3-11 generally illustrate one method of making stent-graft assembly 120, as depicted in FIGS. 1-2. FIG. 3 is a partially exploded view of assembly apparatus 130. Assembly apparatus 130 may comprise tapered dilation mandrel 131, stent retaining mandrel 134 and stent enclosing mandrel 138. Tapered dilation mandrel 131 comprises first end 132 having a tapered diameter and second end 133 wherein the diameter of second end 133 is greater than the tapered diameter. Where other techniques are used to dilate stent 110 and biocompatible graft material, tapered dilation mandrel 131 may not be necessary and thus assembly apparatus 130 may comprise stent retaining mandrel 134 and stent enclosing mandrel 138.

Stent retaining mandrel 134 may be permanently affixed to second end 133 of tapered dilation mandrel 131 or alternatively may be removably coupled to tapered dilation mandrel. For example, stent retaining mandrel 134 may be screwed into tapered dilation mandrel 131 using a screw extending from stent retaining mandrel 134 and a threaded insert embedded into tapered dilation mandrel 131. However, it will be understood by those in the art that couplings are interchangeable and may be any of a wide variety of suitable couplings.

Stent retaining mandrel 134 may comprise a conical region defined by large diameter end 135 and an apex end 136. Large diameter end 135 may be equal in diameter with second end 133 of tapered dilation mandrel 131, and larger in diameter than apex end 136. It is understood that stent retaining mandrel 134 may alternatively be other shapes including non-conical shapes. Stent retaining mandrel 134 may optionally incorporate neck region 137. Neck region 137 may extend from apex end 136, as shown in FIG. 3, and may have the same diameter as apex end 136. Alternatively, neck region 137 may extend from stent enclosing mandrel 138.

Stent enclosing mandrel 138 is removably coupled to stent retaining mandrel 134. For example, stent enclosing mandrel 138 may be screwed into stent retaining mandrel 134 using screw 139 extending from stent enclosing mandrel 138 and threaded insert 140 embedded into stent retaining mandrel 134. Alternatively, screw 139 may extend from stent retaining mandrel 134 and threaded insert may be embedded into stent enclosing mandrel 138. While the figures depict threaded coupling, it will be understood by those skilled in the art that the couplings are interchangeable and may be any of a wide variety of suitable couplings. In another example, stent retaining mandrel 134 may be a female mandrel having a receiving portion and stent enclosing mandrel 138 may be a male mandrel having a protruding portion. However, it is understood that stent retaining mandrel 134 may be a male mandrel having a protruding portion and stent enclosing mandrel 138 may be a female mandrel having a receiving portion.

Stent enclosing mandrel 138 may comprise a conical region defined by large diameter end 142 and an apex end 141, wherein large diameter end 142 is larger in diameter than apex end 141. It is understood that stent enclosing mandrel 138 alternatively take other shapes including non-conical shapes. Stent enclosing mandrel 138 may be permanently affixed to handle segment 144 at large diameter end 142. Alternatively, stent enclosing mandrel 138 may be removably coupled to handle segment 144. Where stent enclosing mandrel 138 is removably coupled to handle segment 144, handle segment 144 may be removed and replaced with a tapered mandrel segment similar to tapered dilation mandrel 131, as shown in FIG. 8C.

Referring to FIG. 4, when coupled together, stent retaining mandrel 134 and stent enclosing mandrel 138 form hourglass shaped mandrel assembly 143. Hourglass shaped mandrel assembly 143 is configured such that the conical region of stent retaining mandrel 134 is oriented toward the conical region of stent enclosing mandrel 138, wherein apex end 136 of stent retaining mandrel 134 having extending neck region 137 is in contact with apex end 141 of stent enclosing mandrel 138. Neck region 137 is configured to conform to the diameter of apex end 136 of stent retaining mandrel 134 and apex end 141 of stent enclosing mandrel 138, whether or not apex end 141 and apex end 136 are equal in diameter. Neck region 137 may vary in diameter or may be eliminated entirely.

The size and shape of hourglass shaped mandrel assembly 143 and specifically the size of the conical regions of stent retaining mandrel 134 and stent enclosing mandrel 138 preferably correspond to the size and shape of first flared region 102, neck region 104 and second flared region 106 of stent 110. Hourglass shaped mandrel assembly 143 may be asymmetrical such that diameter D4 of large diameter end 135 is different than diameter D5 of large diameter end 142. Alternatively, diameter D4 and diameter D5 may be the same. Similarly, angle θ1 and angle θ2 may be different, resulting in an asymmetrical mandrel, or may be the same. Angle θ1 and angle θ2 also may vary along the length of hourglass shaped mandrel assembly 143 to better conform to stent 110. While neck diameter D6 may vary at different points along neck region 137, diameter at neck region 137 is at all times smaller than diameter D4 and D5.

FIGS. 5-7, represents sequential views of first graft tube 122 being loaded onto the tapered dilation mandrel 131 and being concentrically engaged about hourglass shaped mandrel assembly 143 in an exemplary sequence. Engagement of first graft tube 122 over tapered dilation mandrel 131 may be facilitated by forming tabs on first end 153 of first graft tube 122 by cutting longitudinal slits (not shown) along diametrically opposing sides of the graft tube. The tabs may then be used to retain first graft tube 122 while axial force 150 is applied to assembly apparatus 130. Alternatively, the tabs may be used to manually pull first graft tube 122 over tapered dilation mandrel 131 and hourglass shaped mandrel assembly 143. To prevent formation of seams or wrinkles, it is important to avoid applying torsional forces to graft tubes by twisting the graft during engagement of the graft member onto the assembly apparatus. Cutting crevice 151 and 152 may be incorporated into stent retaining mandrel 134 and stent enclosing mandrel 138 to provide a guiding indentation for a cutting element to cut first graft tube 122 and second graft tube 124.

Referring now to FIG. 5, first graft tube 122 may be engaged with tapered dilatation mandrel 131 by applying an axial force 150 to assembly apparatus 130 which causes the tapered dilatation mandrel to pass into and through lumen 154 of first graft tube 122. As first graft tube 122 passes over second end 133 of tapered dilatation mandrel 131, the inner diameter of first graft first 122 is expanded radially to that of the outer diameter of second end 133 of tapered dilation mandrel 131. As first graft tube 122 is moved axially over large diameter end 135 of stent retaining mandrel 134 the inner diameter of first graft tube 122 is greater than the outside diameter of hourglass shaped mandrel assembly 143. Axial force 150 is applied until first end 153 of first graft tube 122 is near large diameter end 142 of stent enclosing mandrel 138. As first graft tube moves axially over second end 133 of tapered dilatation mandrel 131 and is positioned over hourglass shaped mandrel assembly 143, first graft tube 122 undergoes radial recoil so that the inner diameter of first graft tube 122 reduces until it's met with resistance from hourglass shaped mandrel 143. As illustrated in FIG. 6, first graft tube 122 has radially recoiled onto hourglass shaped mandrel assembly 143 as well as into cutting crevices 151 and 152.

FIGS. 6 and 7 illustrate the steps for separating first graft tube 122 and depositing graft layer 170 upon hourglass shaped mandrel 143. Cutting blades 160 and 161 may be used to make circumferential cuts in first graft tube 122 near the large diameter ends of stent retaining mandrel 134 and stent enclosing mandrel 138. For example, cutting blades may make circumferential cuts at the position of cutting crevices 151 and 152. Cutting crevices 151 and 152 are positioned at a length longer than the length of stent 110 to account for recoil of graft material after being cut. Alternatively, where the stent is only partially encapsulated, cutting crevices 151 and 152 may be positioned at a length shorter than the length of stent 110. After cutting first graft tube 122 with cutting blades 160 and 161, first graft layer 170 is deposited onto stent 110. Alternatively, only cutting crevice 151 and cutting blade 160 may be used to create a circumferential cut near the large diameter end of stent retaining mandrel 134. In this manner first end 153 of first graft tube 122 having tabs at the end, may serve as one end of first graft layer 170. First graft layer 170 has a length longer than stent 110. As such, a section of first graft layer 170 extends beyond opposing ends of stent 110. After removing excess grafting material, first graft layer 170 remains on the assembly apparatus and covers hourglass shaped mandrel assembly 143. Tape may be applied to first graft layer 170 to secure graft layer 170 to stent retaining mandrel 134. Upon depositing first graft layer 170 on hourglass shaped mandrel assembly 143, an optional step involves applying a layer of Fluorinated Ethylene Propylene (FEP), or any other adhesive material, to first graft layer 170 for improving adhesion during encapsulation process.

Figure 8A:
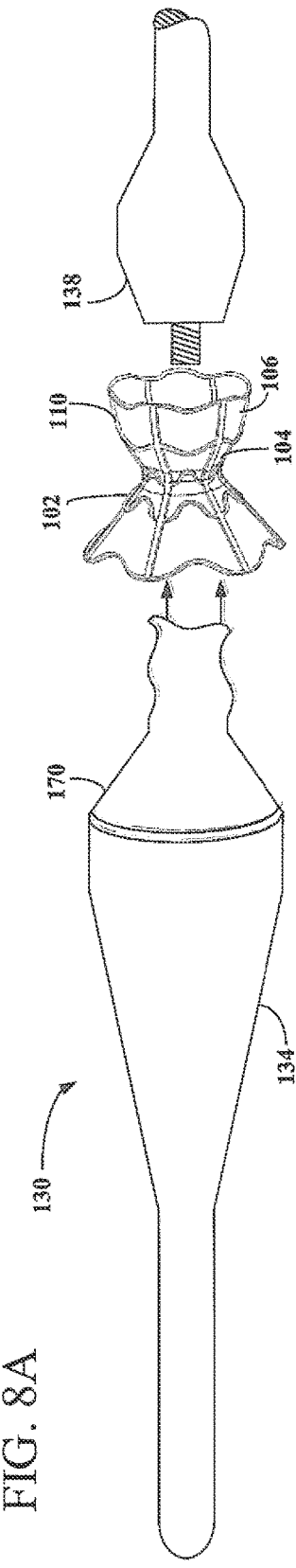
FIGS. 8A-8C are side views of assembly apparatus engaged with first graft layer and hourglass shaped stent.
Figure 8B:
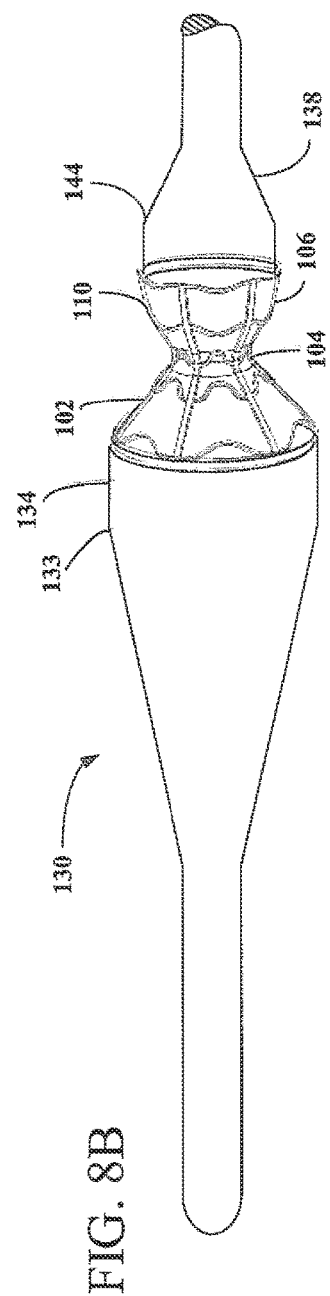
Figure 8C:
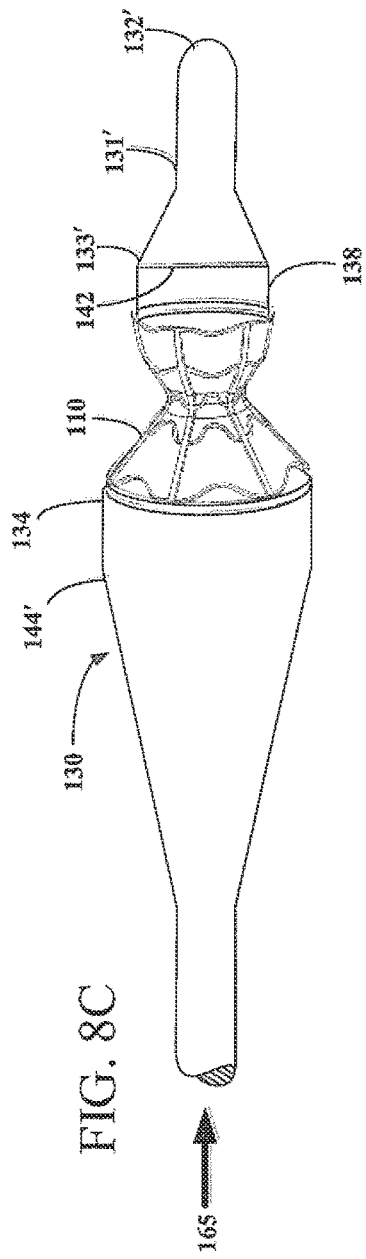

Referring now to FIGS. 8A-8C, after depositing first graft layer 170 on hourglass shaped mandrel assembly 143, stent 110 may be loaded onto hourglass shaped mandrel assembly 143. One method for loading stent 110 onto hourglass shaped mandrel assembly 143 is to uncouple stent retaining mandrel 134 and stent enclosing mandrel 138. When stent retaining mandrel 134 is uncoupled from stent enclosing mandrel 138, the portion of first graft layer 170 in contact with stent retaining mandrel 134 and neck region 137 will remain supported by the stent retaining mandrel 134 but the portion that was in contact with stent enclosing mandrel 138 will become unsupported beyond neck region 137. As shown in FIG. 8A, by uncoupling stent retaining mandrel 134 and stent enclosing mandrel 138, stent 110 may be loaded onto stent retaining mandrel 134 over first graft layer. During this step, the unsupported region of first graft layer 170 may be manipulated in shape and guided through an interior opening of neck region 104 and through an interior of second flared region 106. Where first end 153 of first graft tube 122 is used as the end of first graft layer 170, the tabs on first end 153 of first graft tube 122 described above, may be used to help guide first graft layer 170 through stent 110.

Stent 110 is engaged about the stent retaining mandrel 134 by concentrically positioning the stent 110 over first graft layer 170 and stent retaining mandrel 134. When loaded onto stent retaining mandrel 134, first flared region 102, and neck region 104 of stent 110 engage with stent retaining mandrel 134 while second flared region 106 does not. Stent retaining mandrel 134 and first graft layer 170 are configured to have a combined diameter which is less than the inner diameters of first flared region 102 and neck region 104 of stent 110, allowing stent to slide onto stent retaining mandrel 134.

Referring now to FIG. 8B, upon loading stent 110 on stent retaining mandrel 134 and first graft layer 170, stent enclosing mandrel 138 is coupled to stent retaining mandrel 134, completing the hourglass shaped mandrel assembly. First graft layer 170 may be manually manipulated to avoid being damaged and prevent the occurrence of any wrinkles during recoupling of stent enclosing mandrel 138. For example, first graft layer 170 may be held by the tabs described above while the stent enclosing mandrel is recoupled to the stent retaining mandrel. If first graft layer was taped to stent retaining mandrel 134, the tape may be removed after recoupling. When stent enclosing mandrel 138 is coupled to stent retaining mandrel 134, stent enclosing mandrel 138 engages both first graft layer 170 and second flared region 106 of stent 110, locking stent 110 into position between large diameter end 135 and large diameter end 142. Stent enclosing mandrel 138 and first graft layer 170 are configured to have a combined outside diameter which is less than the inner diameter of second flared region 106 of stent 110, allowing stent 110 to slide into position on stent enclosing mandrel 138. Upon placing stent 110 on first graft layer 170, an optional step involves applying a layer of FEP, or any other adhesive material, to first graft layer 170 and stent 110 for improving adhesion during encapsulation process.

While FIGS. 5-7 illustrate one sequence for generating first graft layer 170, it is appreciated that first graft layer 170 may be deposited onto assembly apparatus 130 in different ways. For example, first graft layer 170 may not be separated from first graft tube 122 until after stent 110 has been loaded onto assembly apparatus 130. In this approach, after first end 153 of first graft tube 122 is positioned near large diameter end 142 of stent enclosing mandrel 138 and first graft tube 122 undergoes radial recoil so that the inner diameter of first graft tube 122 reduces until it is met with resistance from hourglass shaped mandrel 143, as shown in FIG. 6, stent retaining mandrel 134 may be uncoupled from stent enclosing mandrel 138. Like in the sequence described above, the portion of the first graft tube extending beyond neck region 137 will become unsupported after stent enclosing mandrel 138 has been uncoupled. The unsupported region of first graft tube 122 may then be manipulated in shape and guided through an interior opening of neck region 104 and through an interior of second flared region 106 as described above. After the stent enclosing mandrel has been recoupled as shown in FIGS. 8A-8B and discussed above, cuts may be made using cutting blades 160 and 161 to separate first graft tube 122 from first graft layer 170.

In yet another example, first graft layer 170 may be deposited onto hourglass shaped mandrel assembly 143 using an electrospinning process. Electrospinning is a process in which polymers are electrospun into ultrafine fibers which are deposited upon a target surface. The electrospinning process involves applying an electric force to draw fibers out of polymer solutions or polymer melts. Using electrospinning, ultrafine fibers, such as ePTFE fibers may be deposited onto hourglass shaped mandrel assembly 143 to form first graft layer 170. Assembly apparatus may be continuously rotated about its longitudinal axis to evenly apply the ePTFE fibers. In one example, stent retaining mandrel 134 and stent enclosing mandrel 138 may be coupled together during the eletrospinning process. In another example, stent retaining mandrel 134 and stent enclosing mandrel 138 may be uncoupled and the conical region of stent retaining mandrel 134 including neck region 137 may be subjected to the electrospinning process separate from the conical region of stent enclosing mandrel 138. Subsequently, when stent enclosing mandrel 138 and stent retaining mandrel 134 are coupled together, the ePTFE fibers on stent retaining mandrel 134 may be sintered together to form a continuous first graft layer 170. Second graft layer 190 may similarly be deposited using electrospinning.

Referring now to FIG. 8C, assembly apparatus 130 may be configured such that first graft tube 122 and second graft tube 124 may be loaded onto assembly apparatus 130 from the side closest to stent enclosing mandrel 138. As discussed above, stent enclosing mandrel 138 may be removably coupled to handle segment 144. In the alternative configuration shown in FIG. 8C, stent enclosing mandrel 138 may be uncoupled from handle segment 144 and tapered dilation mandrel 131' may be coupled to stent enclosing mandrel 138 instead. It will be understood by those in the art that the couplings are interchangeable and may be any of a wide variety of suitable couplings. Tapered dilation mandrel 131' has first end 132' and second end 133' wherein the diameter of second end 133' is greater than the diameter of first end 132' and the diameter of second end 133' is equal to the diameter of large diameter end 142 of stent enclosing mandrel 138. In the configuration shown in FIG. 8C, large diameter end 135 may also perform as handle segment 144' for pushing.

Using the configuration shown in FIG. 8C, an axial force 165 may be applied to assembly apparatus 130 to cause tapered dilatation mandrel 131' having first end 132' to pass into and through the lumen of the first graft tube 122. Similarly, axial force 165 may be applied to assembly apparatus 130 to guide assembly apparatus 130, and specifically first end 132', into stent 110 which is configured to expand as tapered dilatation mandrel 131' is pushed into stent 110. Axial force 165 may be applied by using handle segment 144' to push assembly apparatus 130. By engaging first end 132' with expandable stent 110 exhibiting spring tension, stent 110 may be dilated as it moves along tapered dilatation mandrel 131'. In this manner, first end region diameter D1, second end region diameter D2, and neck diameter D3 of stent 110, as shown in FIG. 1, may be expanded to a diameter equal to or larger than large diameter end 142 of stent enclosing mandrel 138, thus permitting stent 110 to traverse large diameter end 142. As stent 110 exhibiting spring tension is passed over hourglass shaped mandrel assembly 143, it encounters no resistance to radial recoil and thus radially recoils into position over first graft layer 170 and between large diameter end 135 and large diameter end 142. Alternatively, stent 110 may be expanded to a slightly larger diameter than second diameter end 142 by applying a radially expansive force on stent 110 using an external expansion tool. In this example, after expanding stent 110 to the appropriate diameter, stent 110 may be concentrically placed over stent enclosing mandrel 138 and allowed to radially recoil into position over hourglass shaped mandrel assembly 143 having first graft layer 170 deposited on an outer surface.

In yet another alternative arrangement, stent enclosing mandrel 138 may alternatively be comprised of a cylindrical region instead of a conical region. The cylindrical region may have the same diameter as neck region 137 such that the cylindrical region of stent enclosing mandrel 138 may appear as an extension of neck region 137 when stent enclosing mandrel 138 is coupled to stent retaining mandrel 134. In this alternative embodiment, stent enclosing mandrel 138 also may be coupled to tapered dilation mandrel 131' which may have second end 133' that is equal in diameter to neck region 137 and smaller in diameter than first end 132'. Stent enclosing mandrel 138 having the cylindrical region instead of a conical region, may be used to encapsulate a stent having a conical region and a neck region that forms a conduit. Any of the methods and techniques described herein to encapsulate the hourglass shaped stent may be used to encapsulate the stent having the cylindrical region instead of the conical region. Upon completion of encapsulation, the encapsulated stent may be gently removed from assembly apparatus 130 by sliding the encapsulated stent over the tapered dilation mandrel 131'. Alternatively, stent enclosing mandrel 138 may be uncoupled from stent retaining mandrel 134.

FIGS. 9-11 represent sequential views of the second graft tube 124 being loaded onto the tapered dilation mandrel 131 and being concentrically engaged about stent 110. Engagement of second graft tube 124 over tapered dilation mandrel may be facilitated by forming tabs on first end 171 of second graft tube 124 similar to the method described above, involving cutting longitudinal slits (not shown) along diametrically opposed sides of the graft member. The tabs may then be used to retain the second graft tube 124 while axial force 175 is applied to assembly apparatus 130. Alternatively, the tabs may be used to manually pull second graft tube 124 over tapered dilation mandrel 131 and hourglass shaped mandrel assembly 143.

Referring now to FIG. 9, second graft tube 124 may be engaged with tapered dilation mandrel 131 in much the same way as first graft tube 122—by applying axial force 175 to assembly apparatus 130 which causes the tapered dilation mandrel to pass into and through lumen 173 of second graft tube 124. As second graft tube 124 passes over second end 133 of tapered dilation mandrel 131, the inner diameter of second graft tube 124 is radially expanded to that of the outer diameter of second end 133 of tapered dilation mandrel 131. The assembly apparatus 130 is passed into and through lumen 173 of second graft tube 124 until first end 171 of second graft tube 124 is close to large diameter end 142 of stent enclosing mandrel 138. As second graft tube moves axially over stent 110 and to a position over large diameter end 142 of stent enclosing mandrel 138, second graft tube 124 undergoes radial recoil so that the inner diameter of second graft tube 124 reduces until it is met with resistance. As illustrated in FIG. 10, second graft tube 124 is radially recoiled onto stent 110. Second graft tube 124 also may be radially recoiled into cutting crevices 151 and 152.

Alternatively, second graft tube 124 may be positioned onto stent 110 via an assembly apparatus 130 that is configured to expand and/or contract radially. Assembly apparatus may be comprised of material having expansion properties or contraction properties which may be responsive to exterior conditions. For example, hourglass shaped mandrel assembly 143 may be compressible by applying a force normal to the surface of hourglass shaped mandrel 143. Instead, assembly apparatus 130 may be comprised of material having a high coefficient of thermal expansion permitting the hourglass shaped assembly to contract when placed in a low temperature environment and expand when placed in a high temperature. Alternatively, assembly apparatus may have a rigid core and multiple surfaces that move independently from one another, the surfaces being connected to the core by a number of springs that are configured to permit movement of the surfaces relative to the core when a normal force is applied to the surfaces. For example, a surface may compress towards the core when a normal force is applied and the same surface may expand radially out from the rigid core when the normal force is released. In addition, or alternatively, the core of the assembly apparatus 130 may have a screw assembly embedded within the core and configured to translate a rotational force applied to the screw assembly into a radial force which is applied to the surfaces to push the surfaces radially outward, or pull the surfaces radially inward.

Expandable stent 110 having spring tension may be positioned on compressible hourglass shaped mandrel assembly 143 and stent and assembly together may be compressed when a compressive radial force is applied. At a certain compressive force, first end region diameter D1 and second end region diameter D2 of stent 110 may be compressed to neck diameter D3. In this compressed state, second graft tube 124 may be easily moved axially over compressed stent 110 and first graft layer 170. Subsequent to positioning second graft tube 124 over compressed stent 110 and first graft layer 170, compressive force applied to stent 110 and compressible hourglass shaped mandrel assembly 143 may be released. At the same time, hourglass shaped mandrel assembly 143 may be expanded. In this way second graft tube 124 may be engaged with stent 110.

FIGS. 10 and 11 illustrate the steps for separating second graft tube 124 from stent-graft assembly 120. After depositing second graft tube 124 on stent 110, cutting blades 160 and 161 may again be used to make circumferential cuts in second graft tube 124 at a position near the large diameter ends of stent retaining mandrel 134 and stent enclosing mandrel 138. For example, cutting blades 160 and 161 may make circumferential cuts at the position of cutting crevices 151 and 152. As explained above, cutting crevices 151 and 152 may be positioned at a length longer than the length of stent 110 to account for recoil of graft material upon being cut. After cutting second graft tube 124 with cutting blades 160 and 161, second graft layer 190 is deposited onto stent 110 which is positioned over graft layer 170. Second graft layer 190 has a length longer than stent 110. As such, a section of second graft tube 124 extends beyond opposing ends of stent 110 and is similar in length to first graft layer 170. Waste portion of second graft tube 124 remaining on assembly apparatus 130 may be discarded. Where stent 110 is only partially encapsulated, first graft layer 170 and/or second graft layer 190 may have a length shorter than stent 110 and thus may not extend beyond opposing ends of stent 110. For example, only first flared region 102 or second flared region 106 may be encapsulated. Where stent 110 takes a different asymmetric shape, such as an hourglass shape on one side and a straight tube shape on the other side, only one portion of asymmetric stent 110 may be encapsulated.

To securely bond first graft layer 170 to second graft layer 190, pressure and heat may be applied the stent-graft assembly to achieve sintering. Sintering results in strong, smooth, substantially continuous coating that covers the inner and outer surfaces of the stent. Sintering may be achieved by first wrapping the ends of first graft layer 170 and second graft layer 190 with strips of tape such as TFE or ePTFE tape to secure the stent-graft assembly to the mandrel. To apply pressure, stent-graft assembly 120 attached to assembly apparatus 130 may be placed in a helical winding wrapping machine which tension wraps the stent-graft assembly 120 with at least one overlapping layer of tape. For example, stent-graft assembly 120 may be wrapped with a single overlapping layer of ½ inch ePTFE tape with an overlap of the winding of about 70%. The force exerted by the TFE or ePTFE wrapping tape compresses the stent-graft assembly against the hourglass shaped mandrel assembly 143, thereby causing the graft layers to come into intimate contact through interstices of stent 110. In stent 110 shown in FIG. 1, interstices exist in the between the struts and sinusoidal rings. Varying tape thickness may reduce or improve ePTFE conformance. For example, thicker tape may result in more compression uniformity than thinner tape material.

Stent-graft assembly 120 attached to assembly apparatus 130 may then be heated by placing the stent-graft assembly and assembly apparatus into a radiant heat furnace. For example, stent-graft assembly 120 may be placed into a radiant heat furnace which had been preheated. In one example, sintering may be achieved at 327° C. The humidity within the radiant heat furnace may preferably be kept low. The stent-graft assembly may remain in the radiant heat furnace for a time sufficient for first graft layer 170 to sinter to second graft layer 190. In one example, stent-graft assembly 120 may remain in the furnace for about 7-10 minutes. The heated assembly may then be allowed to cool for a period of time sufficient to permit manual handling of the assembly. After cooling, the helical wrap may be unwound from stent-graft assembly 120 and discarded. The encapsulated stent may then be concentrically rotated about the axis of the mandrel to release any adhesion between the first graft layer 170 and hourglass shaped mandrel assembly 143. The encapsulated stent, still on the mandrel, may then be placed into a laser trimming fixture to trim excess graft materials away from stent-graft assembly 120. In addition, the encapsulated stent may be trimmed at various locations along the stent such as in the middle of the stent, thereby creating a partially encapsulated stent.

Alternatively, first graft layer 170 may be sintered to second graft layer 190 by inducing pressure. For example, assembly apparatus 130 or at least hourglass shaped mandrel assembly 143 may have small perforations which may be in fluid communication with a vacuum pump situated in an inner lumen of assembly apparatus 130 or otherwise in fluid communication with an inner lumen of assembly apparatus 130. Additionally or alternatively, the assembly apparatus 130 may be placed in a pressurized environment that is pressurized using a compressor pump, for example. In another example, a balloon such as a Kevlar balloon may also or alternatively be applied to the exterior of the stent-graft assembly to apply pressure to the stent-graft assembly. Via the pressure applied, the first graft layer 170 may collapse on the second graft layer 190 forming even adhesion. A combination of both pressure and heat may also be used to sinter the first graft layer 170 to the second graft layer 190. Trimming may then take place in the same manner as described above.

After trimming excess graft materials, stent-graft assembly 120 may be removed by decoupling stent retaining mandrel 134 from stent enclosing mandrel 138. Upon decoupling stent retaining mandrel 134 and stent enclosing mandrel 138, stent-graft assembly 120 remains supported by stent retaining mandrel 134. Stent-graft assembly 120 may then be removed from stent retaining mandrel 134 by axially displacing stent-graft assembly 120 relative to stent retaining mandrel 134.

Upon removal of stent-graft assembly 120 from assembly apparatus 130, stent-graft assembly 120 may be manipulated to a reduced first end region diameter D1, second end region diameter D2 and neck region diameter D3. The assembly stent-graft assembly may achieve these smaller diametric dimensions by methods such as crimping, calendering, folding, compressing or the like. Stent-graft assembly 120 may be constrained at this dimension by disposing stent-graft assembly 120 in a similarly sized cylindrical sheath. Once positioned in the sheath, stent-graft assembly 120 may be delivered to an implantation site using a catheter based system including a delivery catheter. The catheter based system may further comprise an engagement component for temporarily affixing stent-graft assembly 120 to the delivery catheter. U.S. Pat. No. 9,713,696 to Yacoby, incorporated herein by reference, describes an exemplary engagement component. The engagement component may be configured to disengage the stent-graft assembly 120 from the delivery catheter when stent-graft assembly 120 has reached the delivery site. At the delivery site, the sheath may be removed to release the constraining force and permit the intraluminal stent to elastically expand in the appropriate position.

While the approach set forth above describes depositing a layer of biocompatible material on an interior surface of stent 110 and an exterior surface of stent 110, it is understood that the stent 110 may be coated with only one layer of biocompatible material. For example, stent 110 may be engaged with only first graft layer 170 along an interior surface, following only the appropriate steps set forth above. Alternatively, stent 110 may be engaged with only second graft layer 190 along an exterior surface, following only the appropriate steps set forth above. It is further understood that only some of the steps described above may be performed and/or one or more of the steps described above may be repeated such that additional or alternative layers of graft or biocompatible material may be deposited upon stent 110. For example, an additional layer(s) may be seamlessly deposited upon stent 110 such that the additional layer(s) is connected to at least one other layer.

As explained above, stent 110 may be comprised of a plurality of sinusoidal rings connected by longitudinally extending struts. However, it is understood that stent 110 may be constructed from a plurality of interconnected nodes and struts having varying distances and forming various shapes and patterns. In one embodiment the inter-nodal-distance (IND) of stent 110 may be manipulated by controlling the tension of the biocompatible material layers during encapsulation. For example, the stent may be encapsulated in a manner providing different pulling forces on stent 110. This may enable different functionality of various areas of the encapsulated stent which are known to be influenced by IND. In one example, by controlling tension of the biocompatible material layers during encapsulation, different functionality of various areas with respect to tissue ingrowth characteristics may be achieved. Further, it is understood that encapsulation may be performed such that stent 110 is constrained in a restricted or contracted state by the encapsulation material. For example, the neck diameter may be decreased from 6 mm to 5 mm. This may permit controlled in-vivo expansion to a fully expanded state using, for example, balloon inflation, whereby the constraint is removed. This procedure may be beneficial in a case where a clinical condition dictates an initial restricted state for delivery but requires a larger unconstrained state for implantation or treatment.

Figure 12A:
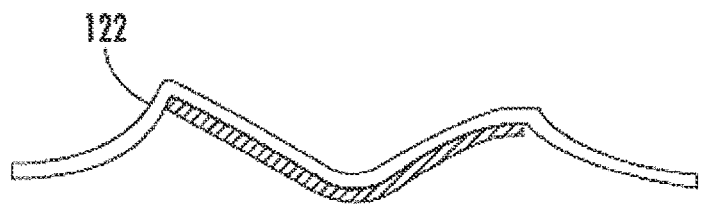
FIGS. 12A-12D are side views sequentially illustrating an encapsulation technique which includes deploying the stent into a sleeve of graft material, and involving a male and female mandrel.

Referring now to FIGS. 12A-D, an alternative method of making stent-graft assembly 120, as depicted in FIGS. 1-2, is illustrated. FIGS. 12A-D represent sequential views of first graft tube 122 and second graft tube 124 being loaded onto and concentrically engaged about stent-graft assembly 120. As shown in FIG. 12A the process may start by engaging first graft tube 122 over stent 110. Stent 110 may be crimped to a diameter smaller than first graft tube 122 and guided into graft tube 122. Alternatively, or in addition to, first graft tube 122 may be stretched to a diameter slightly larger than stent 110 using an expanding mandrel or other stretching technique and guided over stent 110.

Figure 12B:
Figure 12C:
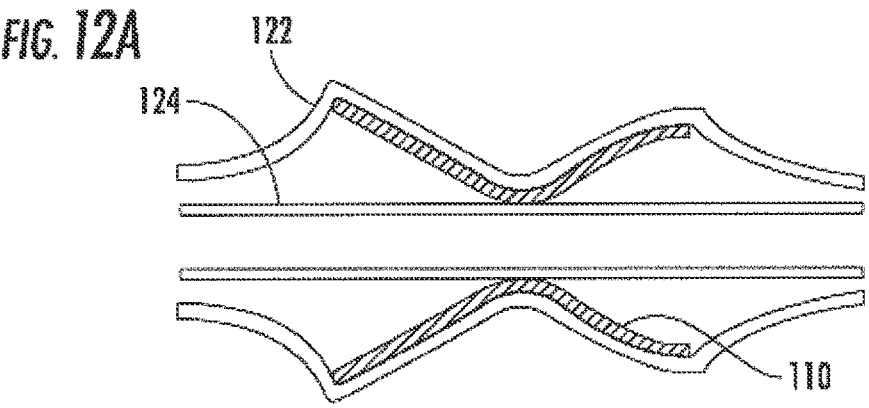

Upon positioning first graft tube 122 over stent 110, second graft tube 124 may be positioned within and along the entire length of stent 110, shown in FIG. 12B. Second graft tube 124 may be pulled through stent 110 while stent 110 remains engaged with first graft tube 122. Second graft tube 124 may optionally be a portion of first graft tube 122 that has been everted at one end and guided through an interior of stent 110. Subsequently, as shown in FIG. 12C, female mandrel 195 may be introduced near second flared region 106 of stent 110. Female mandrel 195 may have a similar shape as second flared region 106 only with slightly smaller dimensions. Female mandrel 195 may have receiving portion 196 designed to receive male mandrel 197. Having a conical shape, female mandrel 195 may be gently advanced within second graft tube 124 until female mandrel 195 takes up nearly the entire space within second flared region 106. In this manner, second graft tube 124 may be engaged with stent 110 along an interior surface of second flared region 106 and, in some embodiments, neck region 104.

Figure 12D:
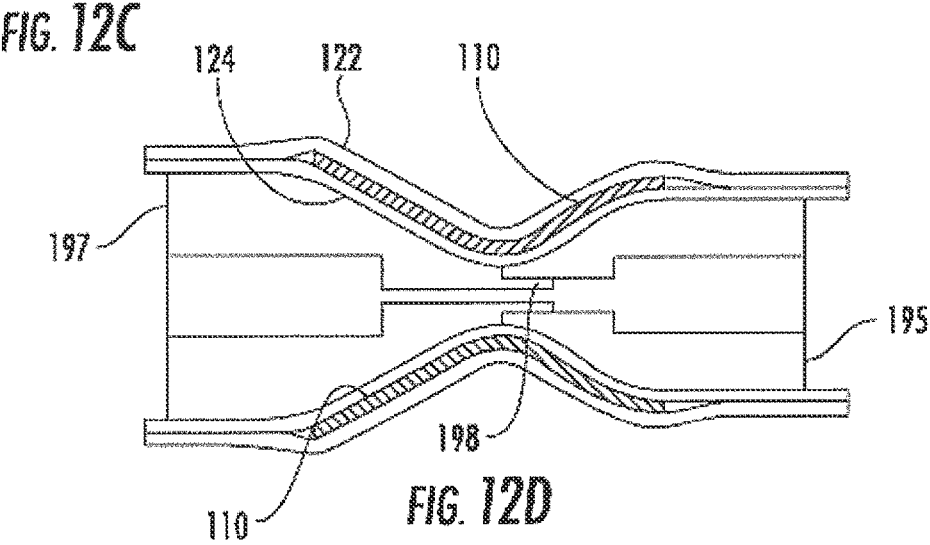

Referring now to FIG. 12D, male mandrel 197 may be introduced near first flared region 102. Male mandrel 197 may be similar in shape to first flared region 102 only with slightly smaller dimensions. Male mandrel 197 may have protruding section 198 sized and shaped to be received by female mandrel 195. Having a conical shape, male mandrel 197 may be gently advanced within second graft tube 124 toward female mandrel 195 until female mandrel 195 takes up nearly the entire space within first flared region 102 and protruding section is fully received by receiving portion 196. In this manner, second graft tube 124 may be engaged with stent 110 along an interior surface of second flared region 106 and, in some embodiments, neck region 104.

Upon engaging female mandrel 195 and male mandrel 197, stent 110 may be entirely covered on an exterior surface by first graft tube 122 and entirely covered on an interior surface by second graft tube 124. First graft tube 122 and second graft tube 124 may be appropriately cut away according to the same procedures illustrated in FIGS. 6 and 10 resulting in first graft layer 170 and second graft layer 190. Further, stent-graft assembly 120 may be produced using the same procedures detailed above including the procedures for securely bonding first graft layer 170 to second graft layer 190 involving pressure and heat applied to the stent-graft assembly to achieve sintering. It is understood that the mandrel placed in the first flared region 102 may alternatively be a female mandrel and the mandrel placed in second flared region 106 may alternatively be a male mandrel. It is also understood that the process depicted in FIGS. 12A-D may start first with the mandrel entering the first flared region 102 of stent 110. It is understood that only some of the steps described above may be performed and/or one or more of the steps described above may be repeated such that additional or alternative layers of graft or biocompatible material may be deposited upon stent 110. For example, an additional layer(s) may be seamlessly deposited upon stent 110 such that the additional layer(s) is connected to at least one other layer.

Figure 13A:
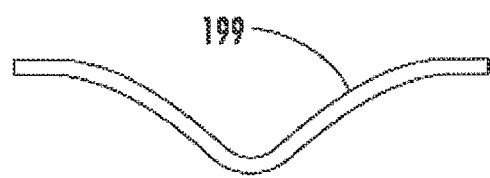
FIGS. 13A-13E are side views sequentially illustrating an encapsulation technique involving pre-shaped grafts and a male and female mandrel.
Figure 13B:
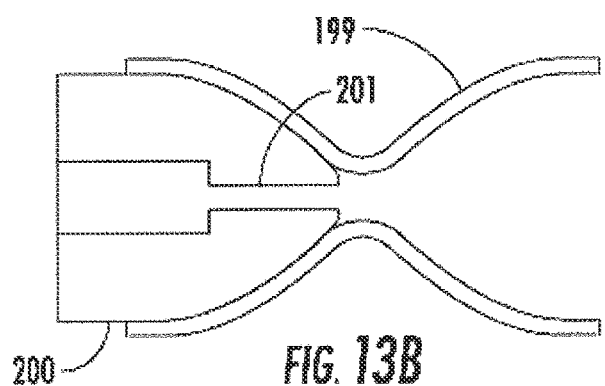

Referring now to FIGS. 13A-13E, another alternative method of making stent-graft assembly 120, as depicted in FIGS. 1-2, is illustrated. As shown in FIG. 13A, first graft layer 170 may be pre-formed into an hourglass shaped pre-formed first graft layer 199 using a dedicated mandrel and heat treatment. The pre-formed shape may have dimensions similar to that of stent 110. Heat may be applied to pre-formed first graft layer 199 to maintain its shape. Upon forming pre-formed first graft layer 199, female mandrel 200 may be introduced into one side of pre-formed first graft layer 199, such that female mandrel 200 takes up nearly the entire space within one hourglass side of pre-formed first graft layer 199 as shown in FIG. 13B. Female mandrel 200 may have receiving portion 201 designed to receive male mandrel 203.

Figure 13C:
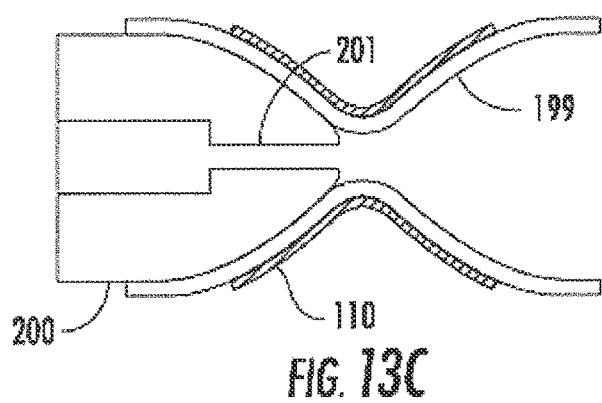

Upon placing female mandrel 200 within pre-formed first graft layer 199, stent 110 may be placed over pre-formed first graft layer 199, as show in in FIG. 13C. Stent 110 may be positioned over pre-formed first graft layer 199 or pre-formed first graft layer 199 may be positioned within stent 110. Stent 110, having a shape similar to that of pre-formed first graft layer 199 should fit into place on pre-formed first graft layer 199.

Figure 13D:
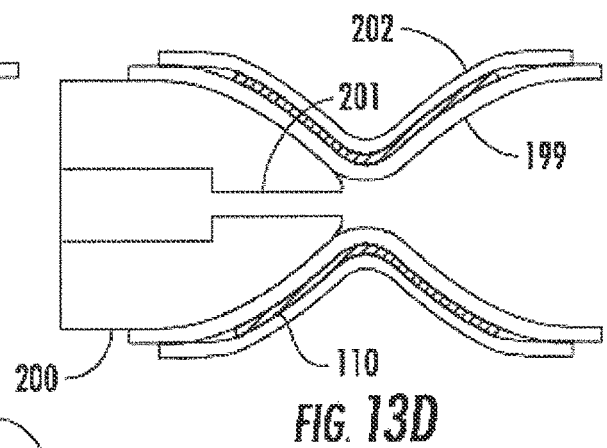

Once stent 110 is deposited on pre-formed first graft layer 199, pre-formed second graft layer 202, formed into an hourglass shape having dimensions similar to stent 110 may be deposited on stent 110 as is illustrated in FIG. 13D. Pre-formed second graft layer 202 may be formed in a similar manner as pre-formed first graft layer 199, using a dedicated mandrel and heat treatment. Pre-formed second graft layer 202 may be expanded and positioned over stent 110. Pre-formed second graft layer 202, may recoil into its pre-shaped form upon releasing any radial expansion force on pre-formed second graft layer 202. Alternatively, or in addition to, stent 110 may be crimped to facilitate mounting of pre-formed second graft layer 202.

Figure 13E:
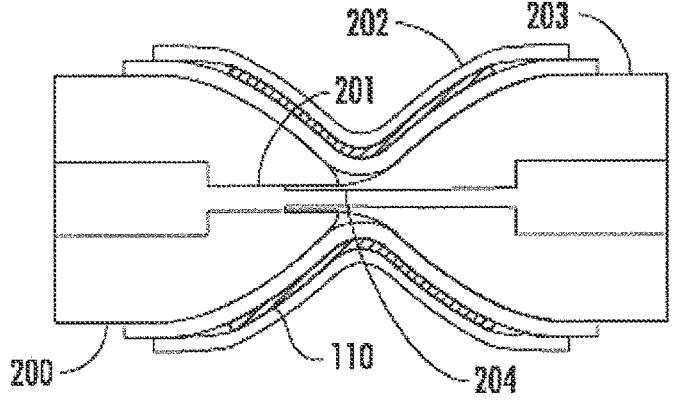

Referring now to FIG. 13E, male mandrel 203 may be introduced near the end of pre-formed first graft layer 199 not occupied by female mandrel 200. Male mandrel 203 may be similar in shape to this end of pre-formed first graft layer 199 only with smaller dimensions. Male mandrel 203 may have protruding section 204 sized and shaped to be received by receiving portion 201 of female mandrel 200. Having a conical shape, male mandrel 203 may be gently advanced within pre-formed first graft layer 199 toward female mandrel 200 until protruding section 204 is fully received by receiving portion 201.

Upon engaging female mandrel 200 and male mandrel 203, stent 110 may be at least partially covered on an exterior surface by pre-formed second graft layer 202 and at least partially covered on an interior surface by pre-formed first graft layer 199. Stent-graft assembly 120 may be produced using the same procedures detailed above including the procedures for securely bonding first graft layer 170, in this case pre-formed first graft layer 199, to second graft layer 190, in this case pre-formed second graft layer 202. These procedures may involve pressure and heat applied to the stent-graft assembly to achieve sintering. This process simplifies the mounting of the graft tubes and reduces risk of tears and non-uniformities. It is understood that the mandrel inserted first into pre-formed first graft layer 199 may alternatively be a male mandrel and the mandrel inserted second may alternatively be a female mandrel. It is further understood that only some of the steps described above may be performed and/or one or more of the steps described above may be repeated such that additional or alternative layers of graft or biocompatible material may be deposited upon stent 110. For example, an additional layer(s) may be seamlessly deposited upon stent 110 such that the additional layer(s) is connected to at least one other layer.

Referring now to FIGS. 14A-14D, another alternative method of making stent-graft assembly 120, as depicted in FIGS. 1-2, is illustrated. As shown in FIG. 14A, the process may start by engaging first graft tube 122 over stent 110. Stent 110 may be crimped using dedicated crimping tools, such as ones detailed in U.S. Pat. No. 9,713,696 to Yacoby, the entire contents of which are incorporated herein by reference, to a diameter smaller than first graft tube 122 and guided into graft tube 122. Alternatively, or in addition to, first graft tube 122 may be stretched to a diameter slightly larger than stent 110 using an expanding mandrel or other stretching mechanism and guided over stent 110. The approach illustrated in FIG. 14A may achieve a firm engagement between crimped stent 110 and the first graft layer 170, enabling improved encapsulation.

Upon positioning first graft tube 122 over stent 110, second graft tube 124 may be positioned within and along the entire length of stent 110, shown in FIG. 14B. Second graft tube 124 may be pulled through stent 110 while stent 110 remains engaged with first graft tube 122. Second graft tube 124 may optionally be a portion of first graft tube 122 that has been everted at one end and guided through an interior of stent 110. Alternatively, stent 110, with first graft tube 122 engaged with stent 110 may be expanded, using well-known expansion techniques, and positioned over second graft tube 124. Subsequently, as shown in FIG. 14C, balloon catheter 205 having inflatable balloon 206 may be inserted into second graft tube 124 such that the balloon catheter 205 is surrounded by stent 110 and first graft tube 122. Alternatively, second graft tube 124 may be positioned over inflatable balloon 206 and inflatable balloon 206 may be positioned within stent 110 via balloon catheter 205.

Referring now to FIG. 14D, upon positioning balloon catheter 205 into second graft tube 124, inflatable balloon 206 of balloon catheter 205 may be inflated to engage second graft tube 124 with an interior surface of stent 110. Using inflatable balloon 206 to engage second graft tube 124 with stent 110 permits uniform contact between and engagement between second graft tube 124 and stent 110 as well as second graft tube 124 and first graft tube 122 between the interstices of stent 110, thus optimizing the adhesion during encapsulation. The degree of inflation may be manipulated to achieve a desired pressure within the balloon and a desired adhesion between first graft tube 122 and the second graft tube 124. Additionally, the degree of inflation may be manipulated to achieve a desired inter-nodal-distance of the graft material. Different pressures may also be achieved by varying the wall thickness of the balloon. Furthermore, interlocking balloons may be used to reduce bond lines.

First graft tube 122 and second graft tube 124 may be appropriately cut away according to the same procedures illustrated in FIGS. 6 and 10 resulting first graft layer 170 and second graft layer 190. Further, stent-graft assembly 120 may be produced using the same procedures detailed above including the procedures for securely bonding first graft layer 170 to second graft layer 190 involving pressure and heat applied to the stent-graft assembly to achieve sintering. It is understood that only some of the steps described above may be performed and/or one or more of the steps described above may be repeated such that additional or alternative layers of graft or biocompatible material may be deposited upon stent 110. For example, an additional layer(s) may be seamlessly deposited upon stent 110 such that the additional layer(s) is connected to at least one other layer.

Figure 15A:
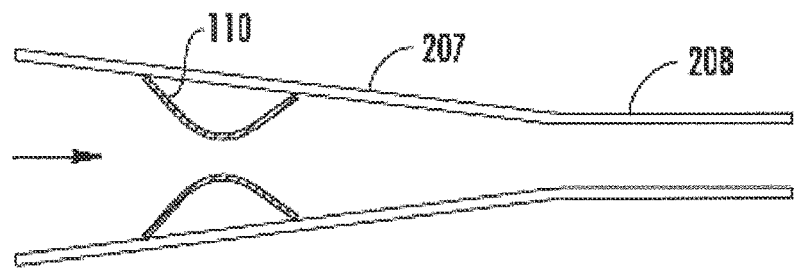
FIGS. 15A-15F are side views sequentially illustrating an encapsulation technique involving a funnel, a single graft material sleeve, and a male and female mandrel.

Referring now to FIGS. 15A-15F, another alternative method of making stent-graft assembly 120, as depicted in FIGS. 1-2, is illustrated. As shown in FIG. 15A, the process may start by placing stent 110 within funnel 207 and advancing stent 110 within funnel 207 towards a reduced section of funnel 207, using, for example, a dedicated pusher tool like the one described in U.S. Pat. No. 9,713,696 to Yacoby, to reduce the diameter of stent 110. Stent 110 may be constructed in a manner that, upon reduction caused by funnel 207, the shape of stent 110 morphs such that the flared ends are tapered and eventually turned inward toward a longitudinal axis of stent 110, resulting in stent 110 having a substantially reduced cross-sectional diameter.

Figure 15B:
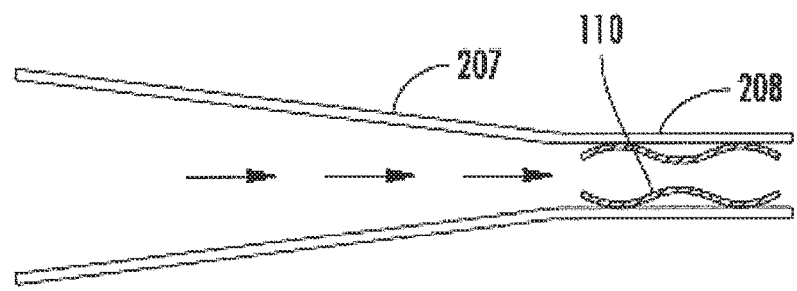
Figure 15C:
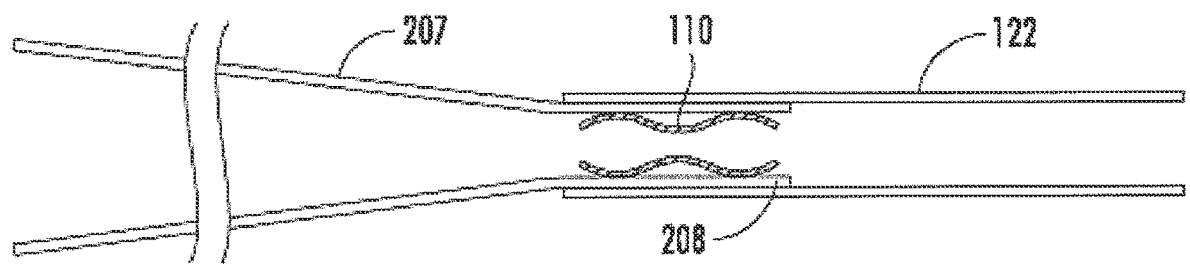

As is shown in FIG. 15B, funnel 207 may have introducer tube 208 extending from the narrow side of the funnel 207 which may receive stent 110 after stent 110 has been fully restricted by funnel 207. It is understood that tube 208 and funnel 207 may be the same component or may be different components that are coupled together (e.g., screwed together). Introducer tube 208 may have a diameter smaller than that of first graft tube 122. Introducer tube may thus be inserted into first graft tube 122, as is illustrated in FIG. 15C, and stent 110 having the reduced diameter, may be advanced out of introducer tube 208 and into first graft tube 122. Alternatively, it is understood that introducer tube 208 may have a diameter the same size as or larger than that of graft tube 122 and graft tube 122 may be stretched and mounted over introducer tube 208.

Figure 15D:
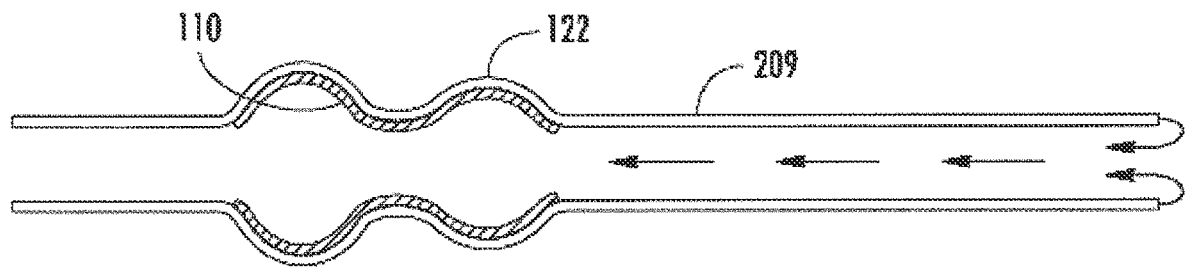

Referring now to FIG. 15D, stent 110 is illustrated after having been advanced from introducer tube 208 and into first graft tube 122. As is shown in FIG. 15D, upon the removal of inward radial force from introducer tube 208, stent 110 may expand radially to a diameter larger than the diameter of first graft tube 122, thereby engaging first graft tube 122 along the outer surface of stent 110. An end of first graft tube 122 may have been positioned a distance beyond introducer tube 208 such that upon depositing stent 110 into first graft tube 122, remaining portion 209 of first graft tube 122 extends beyond stent 110 a distance of more than one length of stent 110.

Figure 15E:
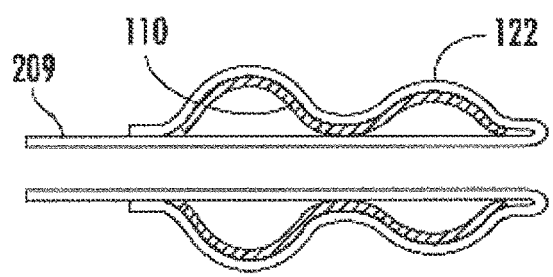
Figure 15F:
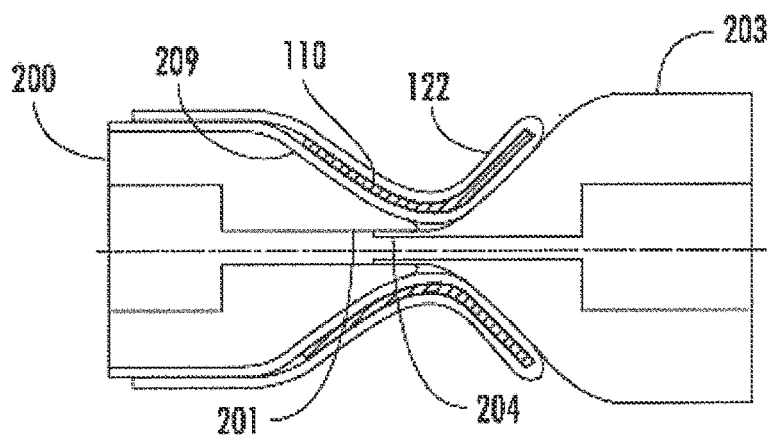

Referring now to FIG. 15E, remaining portion of first graft tube 122 may be used as a second graft layer along the internal surface of stent 110 by pushing remaining portion 209 through the interior of stent 110 and out an opposing side of stent 110, in the direction indicated by the arrows in FIG. 15D. Specifically, as is shown in FIGS. 15D and 15E, first graft tube 122 may be everted at one end and guided through an interior of stent 110 such that remaining portion 209 is positioned within the interior of stent 110. In this manner, first graft tube 122 may extend along an exterior surface of stent 110, curve around an end of stent 110 and travel along the interior of stent 110.

To engage remaining portion 209 with the interior surface of stent 110, female mandrel 200 having receiving portion 201 and male mandrel 203 having protruding section 204 may be inserted into the stent-graft combination. Female mandrel 200 may be introduced first to one end of the stent-graft combination having a size slightly larger than the dimensions of female mandrel 200. Subsequently, male mandrel 203 may be introduced into the opposing end of the stent-graft combination and advanced until protruding section 204 is received by receiving portion 201. As female mandrel 200 and male mandrel 203 are inserted, stent 110 may be guided into its original hour-glass shape. This method may induce improved adhesion between first graft tube 122, remaining portion 209 and stent 110.

Upon engaging female mandrel 200 and male mandrel 203, first graft tube 122 and remaining portion 209 may be appropriately cut away according to the same procedures illustrated in FIGS. 6 and 10 resulting first graft layer 170 and second graft layer 190, with the exception that only one side of stent-graft assembly 120 needs to be cut or otherwise removed first graft tube 122 and remaining portion 209. Stent-graft assembly 120 may be produced using the same procedures detailed above including the procedures for securely bonding first graft layer 170 to second graft layer 190 involving pressure and heat applied to the stent-graft assembly to achieve sintering. It is also understood that the process depicted in FIG. 15F may start with the male mandrel entering the stent-graft combination first. It is further understood that only some of the steps described above may be performed and/or one or more of the steps described above may be repeated such that additional or alternative layers of graft or biocompatible material may be deposited upon stent 110. For example, one or more of the steps described above may be repeated to deposit fourth, five, or sixth layers upon stent 110. The additional layer(s) may be seamlessly deposited upon stent 110 such that the additional layer(s) is connected to at least one other layer.

Figure 16A:
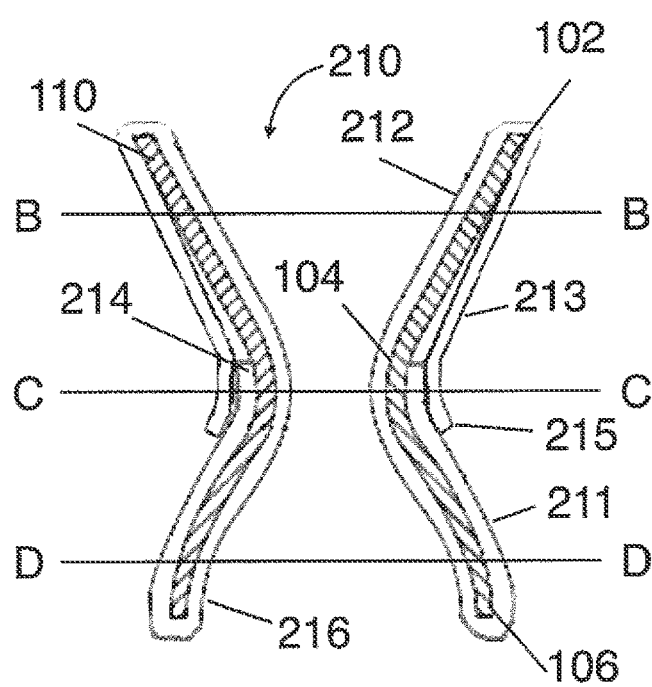
FIGS. 16A-16D illustrate the structure of the stent-graft assembly having two and three layer regions.

Referring now to FIGS. 16A-D, stent 110 may alternatively be covered with a single tube of biocompatible material, as shown in FIG. 16A, to create stent-graft assembly 210 having varying layers of biocompatible material (e.g., two-to-three layers of biocompatible material). Graft tube 216, which is a tube of biocompatible material, has first graft portion 211, second graft portion 212, and third graft portion 213. Graft tube 216 has a length that is longer that the length of stent 110 and preferably greater than twice the length of stent 110. First graft portion 211 begins at first end 214 of graft tube 216 and extends to second graft portion 212. Second graft portion 212 extends between first graft portion 211 and third graft portion 213 and is continuously joined to first graft portion 211 and third graft portion 213. Third graft portion 213 ends at second end 215 of graft tube 216. FIGS. 17A-22B illustrate an exemplary approach for depositing graft tube 216 on stent 110 in the configuration shown in FIGS. 16A-D.

Figure 16B:
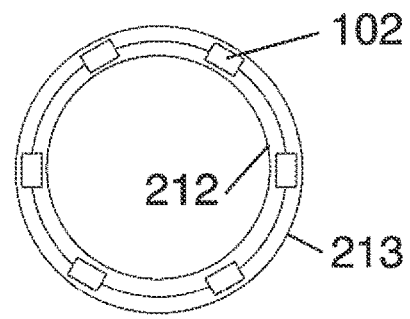
Figure 16C:
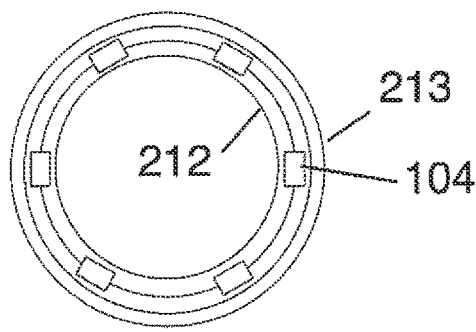
Figure 16D:
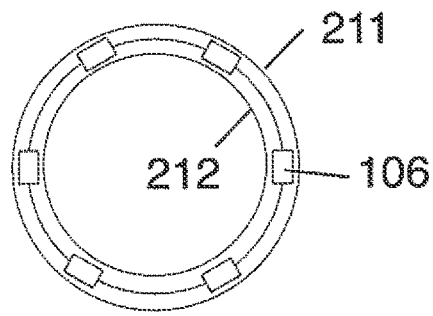

The cross sections of stent-graft assembly 210 illustrated in FIG. 16A (cross-sections B, C, and D) are illustrated in FIGS. 16B, 16C, and 16D, respectively. Referring now to FIG. 16B, cross-section B of stent-graft assembly 210 is illustrated. As is shown in FIG. 16B, first flared region 102 of stent 110 is covered on the inside and outside by graft tube 216. Specifically, first flared region 102 is covered on the outside by third graft portion 213 and on the inside (i.e., on the interior of first flared region 102) by second graft portion 212. Accordingly, stent 110 is covered at first flared region 102 by two layers of biocompatible material.

Referring now to FIG. 16C, cross-section C of stent-graft assembly 210 is illustrated. As is shown in FIG. 16C, neck region 104 of stent 110 is covered by two layers of biocompatible material on the outside and one layer of biocompatible material on the inside. Specifically, stent 110 is first covered on outside by first graft portion 211, which is covered by third graft portion 213. On the inside (i.e., on the interior of neck region 104), stent 110 is covered by second graft portion 212. Accordingly, stent 110 of stent-graft assembly 210 is covered at neck region 104 by three layers of biocompatible material.

Referring now to FIG. 16D, cross-section D of stent-graft assembly 210 is illustrated. As is shown in FIG. 16D, second flared region 106 of stent 110 is covered on outside and inside by graft tube 216. Specifically, first flared region 102 is covered on the outside by first graft portion 211 and on the inside (i.e., on the interior of second flared region 106) by second graft portion 212. Accordingly, stent 110 of stent-graft assembly 210 is covered at second flared region 106 by two layers of biocompatible material.

As also discussed below, the layers of biocompatible material may be securely bonded together to form a monolithic layer of biocompatible material. For example, first graft portion 211, second graft portion 212, and third graft portion 213 may be sintered together to form a strong, smooth, substantially continuous coating that covers the inner and outer surfaces of the stent. Portions of the coating may then be removed as desired from selected portions of the stent using laser-cutting or mechanical cutting, for example.

Figure 17A:
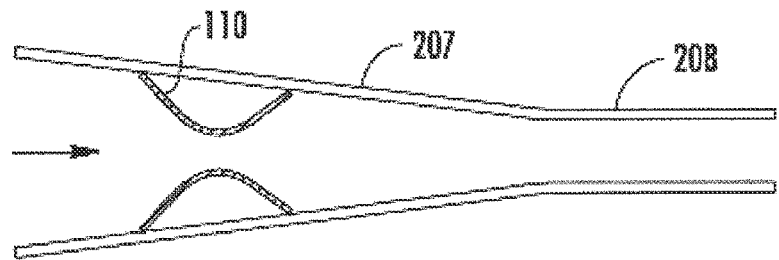
FIGS. 17A-17E are side views sequentially illustrating a technique of depositing a first graft portion on a stent.

FIGS. 17A-22D generally illustrate an exemplary method of making stent-graft assembly 210, as depicted in FIGS. 16A-D. Referring now to FIG. 17A, to deposit the first graft portion upon the neck region and the second flared region, the process may start by crimping stent 110. For example, stent 110 may be placed within funnel 207 and advanced within funnel 207 towards a reduced section of funnel 207. The reduced section preferably is the diameter of the neck region of the stent or slightly larger. However, it is understood that stent 110 may be reduced to different diameters. As explained above with reference to FIG. 15A, stent 110 may be advanced by a dedicated pusher tool like the one described in U.S. Pat. No. 9,713,696 to Yacoby. As also explained above, stent 110 may be constructed in a manner that, upon reduction caused by funnel 207, the shape of stent 110 morphs such that the flared ends are tapered and eventually turned inward toward a longitudinal axis of stent 110, resulting in stent 110 having a substantially reduced cross-sectional diameter. It is understood that stent 110 may alternatively be compressed into a compressed state using any well-known compressing or crimping techniques.

Figure 17B:
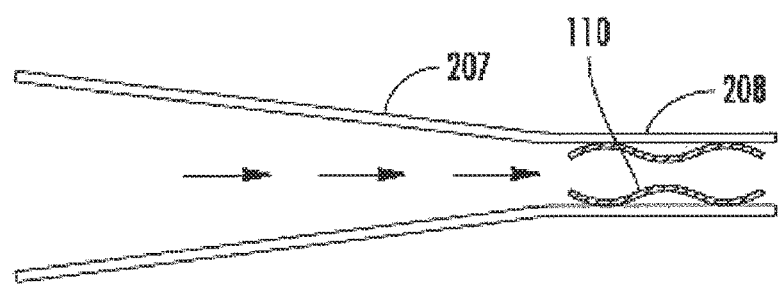
Figure 17C:
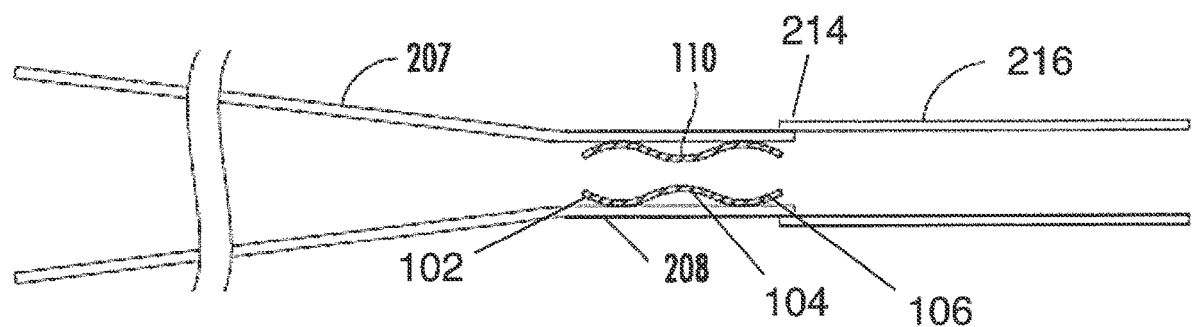

As is shown in FIGS. 17B and 17C, funnel 207 may have or may be coupled to introducer tube 208 extending from the narrow side of the funnel 207 which may receive stent 110 after stent 110 has been fully restricted by funnel 207. Introducer tube 208 may have a diameter smaller than that of the graft tube. Alternatively, the first end of the graft tube may be expanded to a diameter larger than that of introducer tube 208 using well-known expansion techniques (e.g., applying heat to the graft tube). Introducer tube 208 may thus be inserted into first end 214 of graft tube 216, as is illustrated in FIG. 17C, and stent 110 having the reduced diameter, may be partially advanced out of introducer tube 208 and into graft tube 216, such that second flared region 106 and neck region 104 are advanced into graft tube 216.

Figure 17D:
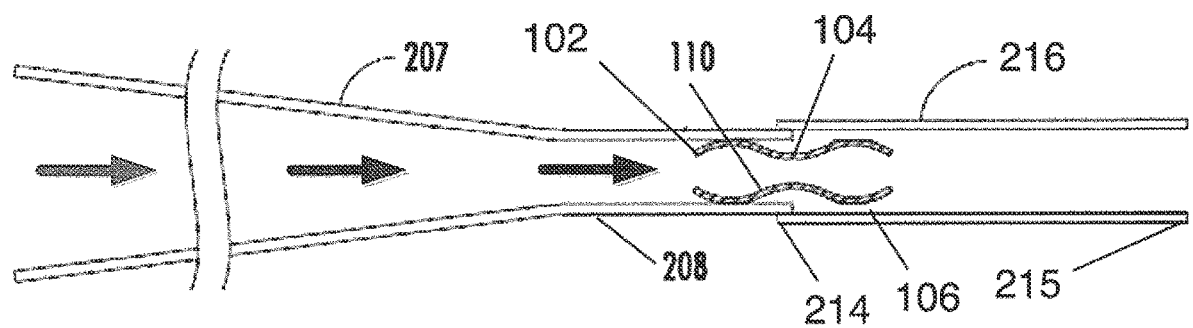

Referring now to FIG. 17D, second flared region 106 and neck region 104 of stent 110 are illustrated after having been advanced from introducer tube 208 and into graft tube 216 thereby releasing compressive force on second flared region 106 and neck region 104, if any. Upon the removal of inward radial force from introducer tube 208, at least second flared region 106 of stent 110 may expand radially to a diameter larger than the diameter of graft tube 116, thereby engaging graft tube 116 along the outer surface of second flared region 106 and neck region 104 in a manner that causes graft tube 216 to expand in an unstressed and unwrinkled fashion. To increase the elasticity of graft tube 216 to permit stent 110 to expand to its expanded state, heat may be applied to both graft tube 216 and stent 110. For example, heated air may be directed at graft tube 216 and stent 110. In an alternative approach, stent 110 may be cooled below its martensite-to-austenite transformation temperature, such that it becomes martensite. Graft tube 116 may be loaded onto second flared region 106 and neck region 104 in this contracted state and permitted to slowly expand as stent 110 warms to room temperature or an elevated temperature in a manner that causes graft tube 216 to expand in an unstressed and unwrinkled fashion.

Figure 17E:
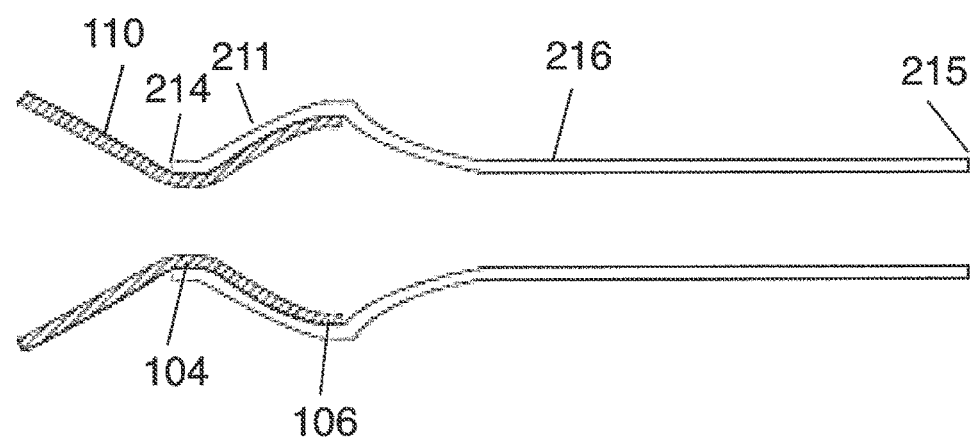

Referring now to FIG. 17E, after depositing first graft portion 211 of graft tube 216 upon second flared region 106 and neck region 104, stent 110 may be completely ejected from introducer tube 208, thereby releasing any compressive force on first flared region 102. Upon being ejected from introducer tube 208, and/or in response to an expandable, stent 110 may expand and return to the expanded state illustrated in FIG. 17E.

Graft tube 216 may be cut or otherwise manufactured to be the length required to extend along stent 110 starting at the exterior surface of neck region 104 adjacent to first flared region 102, along the exterior surface of neck region 104 and second flared region 106, along the interior surface of stent 110 and over the exterior surface of first flared region 102 and neck region 104, terminating at the neck region adjacent to second flared region 106. Alternatively, graft tube 216 may be longer than desired and may be cut using well-known cutting techniques (e.g., micro-scissors, material cutting guillotine or laser-cutting machine) to achieve the desired length after the approach described with respect to FIGS. 17A-22D has been performed.

Figure 18A:
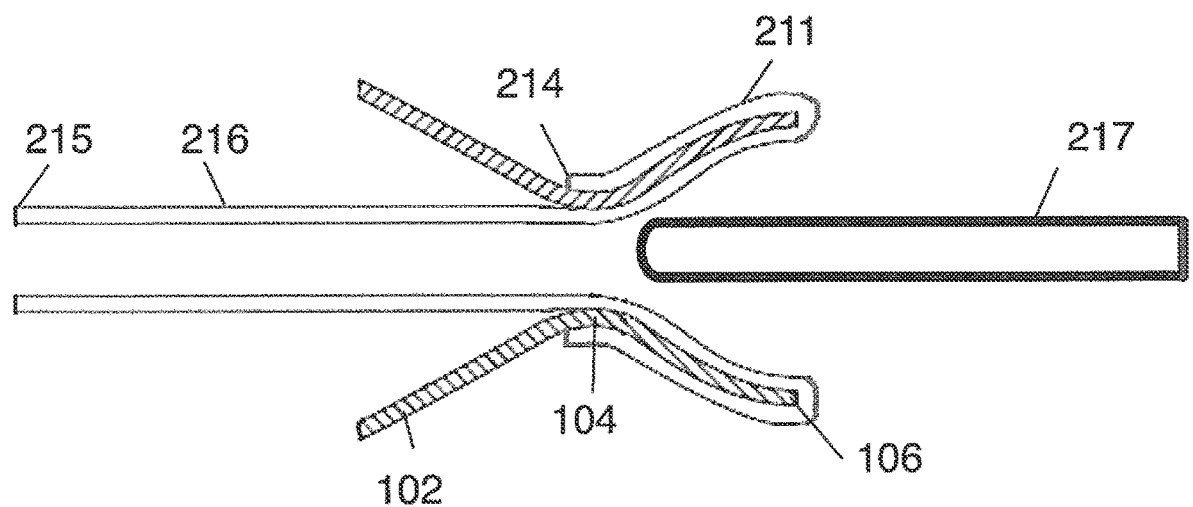
FIGS. 18A-18B are side views sequentially illustrating a technique of depositing a second graft portion on a stent.

Referring now to FIG. 18A, to deposit graft tube 216 along the interior of stent 110, graft tube 216 may be guided through the interior of stent 110, as shown in FIG. 18A. As shown in FIG. 18A, graft tube 216 may be everted at one end and guided through an interior of stent 110 such that the everted portion of graft tube 216 is positioned within the interior of stent 110. To facilitate this process plunger 217, which may be any tool having a long shaft and a width or diameter less than the inner diameter of neck region 104 in the expanded state, may be used to push graft tube 216 through the interior of stent 110. In this manner, first graft portion 211 may extend along an exterior surface of second flared region 106, curve around the end of second flared region 106 and travel along the interior of stent 110 and out an opposing side of stent 110.

Figure 18B:
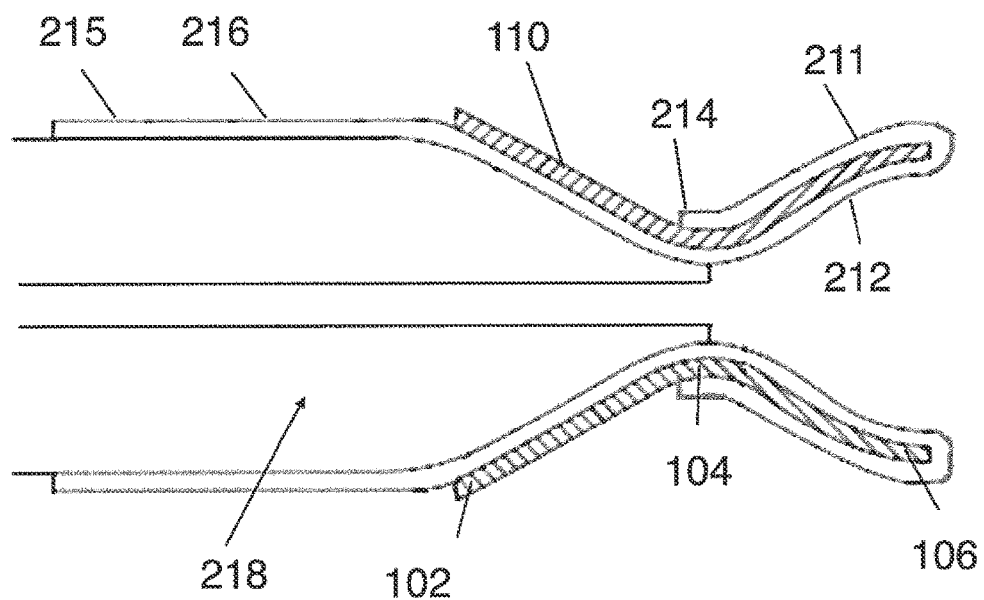

Referring to FIG. 18B, to engage remaining portion of second graft portion 212 with the interior surface of stent 110, first mandrel portion 218 may be engaged with stent 110 and second graft portion 212. Having an end-shape formed to correspond to the interior of first flared region 102, first mandrel portion 218 may be gently advanced within second end 215 of graft tube 216 and stent 110 until first mandrel portion 218 takes up nearly the entire space within first flared region 102. This process may involve guiding first flared region 102 onto first mandrel portion 218 while simultaneously guiding second end 215 of graft tube 216 over first mandrel portion 218 such that second end 215 of the graft tube 216 extends along first mandrel portion 218 in a manner that is tight fitting and free from wrinkles. When first flared region 102 is properly mounted upon first mandrel portion 218, second end 215 of graft tube 216 will extend beyond the first flared region 102, as is shown in FIG. 18B. In this manner, second graft portion 212 may be partially engaged with stent 110 along an interior surface of stent 110.

Figure 19A:
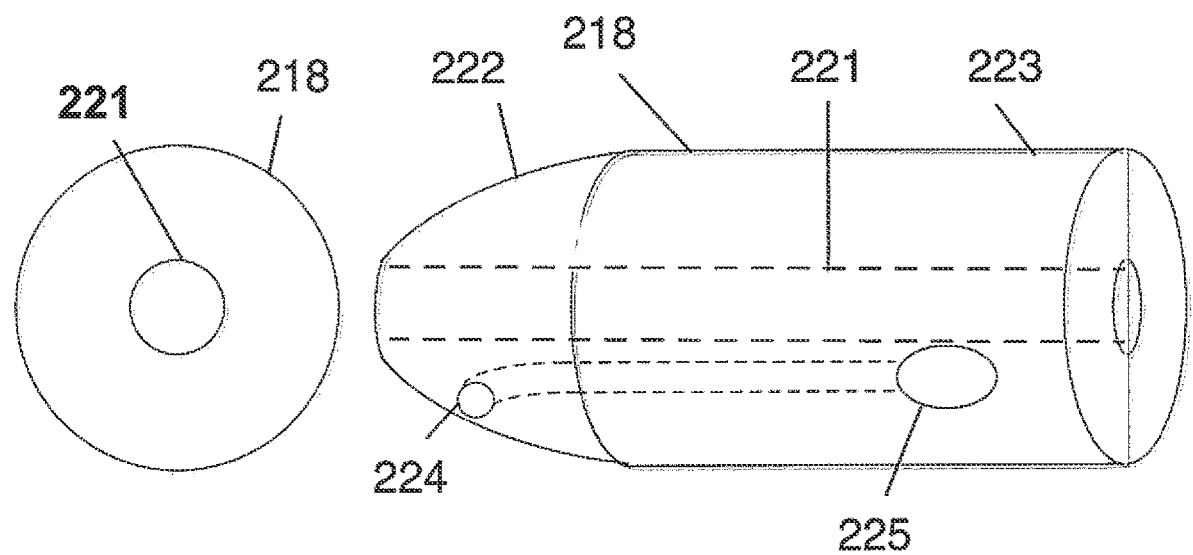
FIGS. 19A-19B illustrates the mandrel assembly including the first mandrel portion illustrated in FIG. 19A and the second mandrel portion illustrated in FIG. 19B.
Figure 19B:
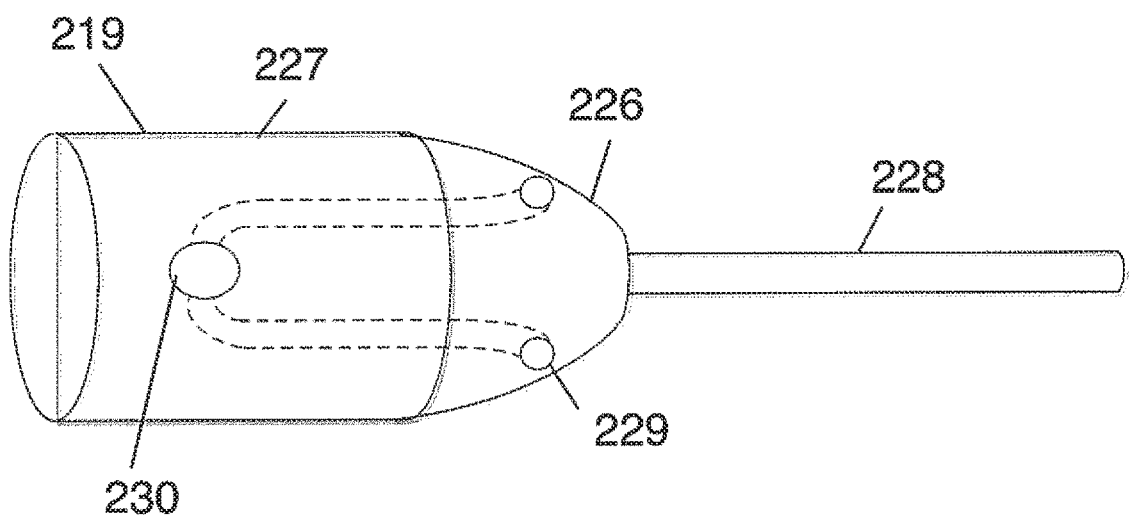
Figure 20A:
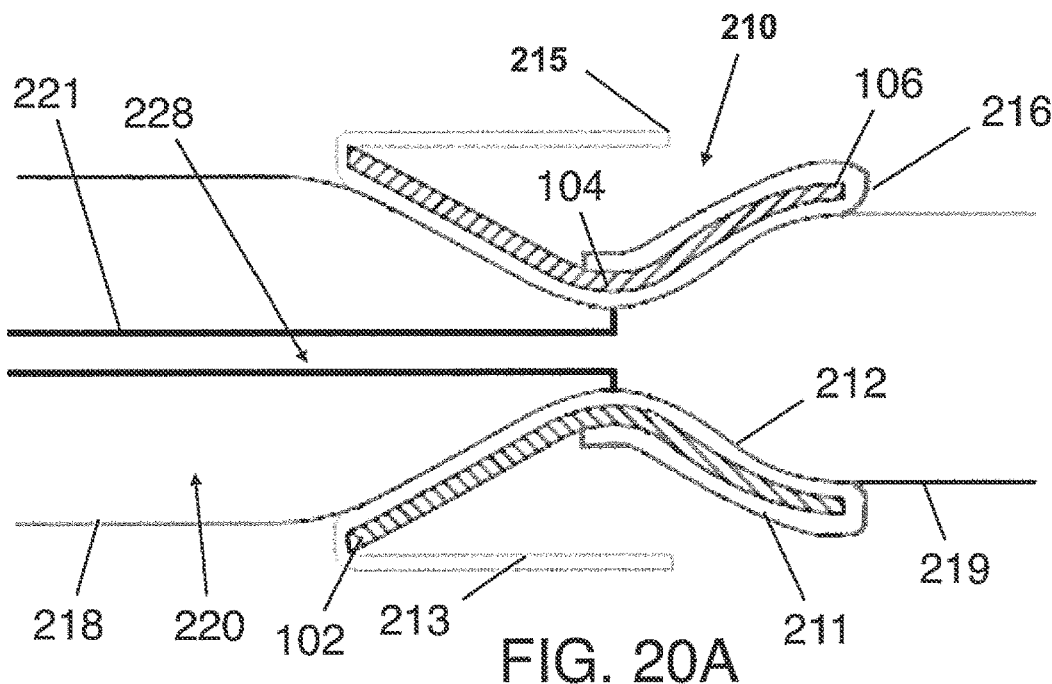
FIGS. 20A-20C are side views and a close-up view illustrating a technique of depositing a third graft portion on a stent.
Figure 20B:
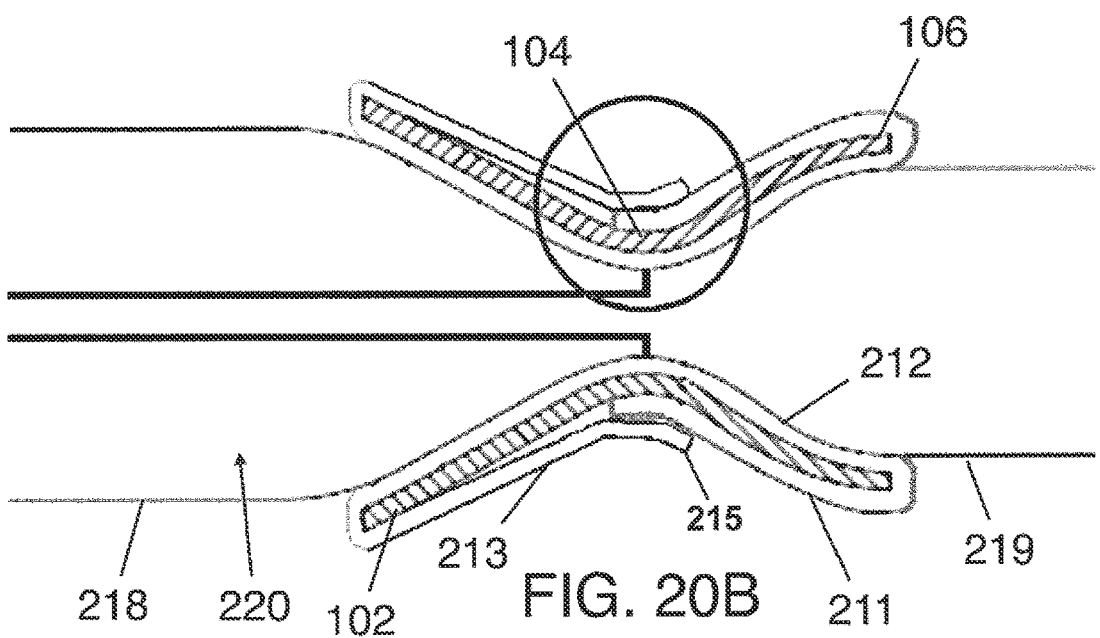

Referring now to FIGS. 19A-19B, first mandrel portion 218 (FIG. 19A) and second mandrel portion 219 (FIG. 19B) are illustrated. As is illustrated in FIGS. 20A-20B, first mandrel portion 218 and second mandrel portion 219 may be removably coupled to form mandrel assembly 220. Referring now to FIG. 19A, a side view and head-on view of first mandrel portion 218 is illustrated. First mandrel portion 218 may have first retention portion 222 and first body portion 223, where first retention portion 222 extends from first body portion 223. First retention portion 222 is designed to engage with stent-graft assembly 210 and have a similar shape as the first flared region and/or the neck region only with slightly smaller dimensions. First body portion 223 may have a cylindrical shape. It is understood that first mandrel portion may alternatively only have first retention portion 222. First mandrel portion 218 may have receiving portion 221 sized and configured to receive protruding portion 228 of second mandrel portion 219. Receiving portion 221 may extend the entire length of first mandrel portion 218 or may alternatively only extend a portion of first mandrel portion 218.

First mandrel portion 218 may also, optionally, have one or more ventilation holes 224 in first retention portion 222. Ventilation holes 224 may extend through an exterior surface of first retention portion 222 and may tunnel through the interior of first retention portion 222 and first body portion 223 to ventilation inlet 225 which may extend through the surface of first body portion 223. Ventilation holes 224 are preferably in the range of 0.1-2 mm in size, though it is understood that ventilation holes of different sizes may beneficial. Ventilation holes 224 may facilitate release of stent-graft assembly 210 after the heat treatment is applied, as explained below with respect to FIGS. 22A-B. Specifically, after the encapsulated stent is tightly compressed against mandrel assembly 220, and the air between the encapsulated stent and mandrel assembly 220 is vacated, there may exist a suction force making it difficult to remove the encapsulated stent. Ventilation inlet 225 may permit air to flow through ventilation inlet to ventilation holes 224 to eliminate or reduce the suction effect. It is understood that multiple ventilation holes may communicate with one or more ventilation inlets.

Referring now to FIG. 19B, second mandrel portion 219 is illustrated. Second mandrel portion 219 may have second retention portion 226 and second body portion 227, where second retention portion 226 extends from second body portion 227. Second retention portion 226 is designed to engage with stent-graft assembly 210 and may have a similar shape as the second flared region and/or the neck region only with slightly smaller dimensions. Second body portion 227 may have a cylindrical shape. It is understood that second mandrel portion may alternatively only have second retention portion 226.

Second mandrel portion 219 has protruding portion 228 sized and shaped to be received by receiving portion 221 of first mandrel portion 218. Protruding portion 228 may be, for example, a shaft that extends from second retention portion 226. Protruding portion may be coaxial with second mandrel portion 219 and may be designed to extend part of the length, the entire length or more than the length of first mandrel portion 218. Like first mandrel portion 218, second mandrel portion 219 may, optionally, include one or more ventilation holes 229 and one or more ventilation inlets 230.

Referring now to FIG. 20A, to constrain stent-graft assembly 210 on mandrel assembly 220, second mandrel portion 219 is removably coupled with first mandrel portion 218 by engaging protruding portion 228 with receiving portion 221. Second mandrel portion 219 may be gently advanced within second flared region 106 of stent-graft assembly 210 toward first mandrel portion 218 until second mandrel portion 219 takes up nearly the entire space within second flared region 106 and protruding portion 228 is fully received by receiving portion 221. In this manner, second graft portion 212 may be fully engaged with second flared region 106.

Protruding portion 228 may be designed to engage with receiving portion 221 such that protruding portion 228 and engagement portion are releasably locked together. Alternatively, protruding portion 228 may be design to friction fit within receiving portion 221. For example, protruding portion may be designed with a gradually increasing diameter that may result in a friction fit with receiving portion 221. In this example, first mandrel portion 218 and second mandrel portion 219 may be released by forcibly pulling first mandrel portion 218 and second mandrel portion 219 apart. It is understood that first mandrel portion 218 and second mandrel portion 219 may be releasably locked together or otherwise friction fit together using various other well-known techniques. It is further understood that protruding portion 228 may instead extend from first mandrel portion 218 and receiving portion 221 may instead be formed within second mandrel portion 219.

As is shown in FIG. 20A, after engaging second mandrel portion 219 with first mandrel portion 218, and thus constraining stent-graft assembly 210 on mandrel assembly 220, third graft portion 213 may be separated from the surface of first mandrel portion 218. For example, forceps may be used to grasp second end 215 of graft tube 216 and gently pull second end 215 over first flared region 102 and over neck region 104. In this manner, graft tube 216 may be everted and guided over first flared region 102 and over neck region 104. Alternatively, other well-known techniques may be used for separating third graft portion 213 from first mandrel portion 218 and depositing third graft portion 213 over first flared region 102 and neck region 104.

Referring now to FIG. 20B, third graft portion 213 may gently be compressed against first flared region 102 and neck region 104 in a manner that reduces or eliminates wrinkles. For example, second end 215 may be manually stretched using forceps toward neck region 104 and gently permitted to make contact with first flared region 102 and the portion of first graft portion 211 in contact with neck region 104.

Figure 20C:
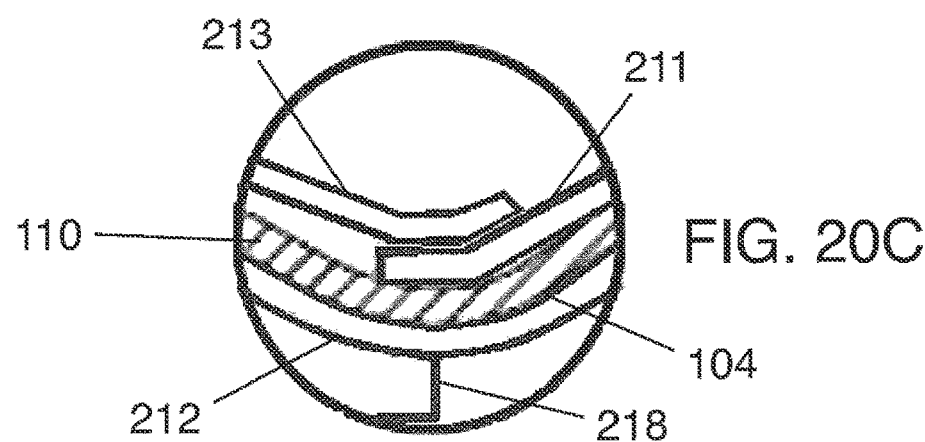

By placing third graft portion 213 over first flared region 102 and neck region 104, graft tube 216 will be deposited over stent 110 such that graft tube 216 covers stent 110 in the manner depicted in FIGS. 16A-16D. As is shown in FIG. 20C, depositing graft tube 216 over stent 110 in the foregoing manner results in three biocompatible layers of graft material covering neck region 104 of stent 110. Specifically, as is shown in FIG. 20C, neck region 104 of stent 110 is covered on an interior surface by second graft portion 212 and is covered on an exterior surface by first graft portion 211 and third graft portion 213. In FIG. 20C, third graft portion 213 overlaps first graft portion 211 at neck region 104. As is shown in FIGS. 16B and 16D, first flared region 102 and second flared region 106 of stent 110 may only be covered by two layers of biocompatible material. In this manner, second graft portion 212 may extend through a lumen of stent 110 through the first end of first flared region 102, through neck region 104, and to the end of second flared region 106; first graft portion 211 extends along an exterior of second flared region 106 and neck region 104; and third graft portion 213 extends along an exterior of first flared region 102 and neck region 104, overlapping, at least partially, and joining with first graft portion 211.

It is understood that graft tube 216 may be deposited upon stent 110 to form stent-graft assembly 210 having the same three-layer structure at the neck region 104 and two-layer structure at first flared region 102 and second flared region 106 using different approaches than the approach detailed in FIGS. 17A-20C. For example, graft tube 216 may first be guided through the interior of stent 110. First end 214 and second end 215 may then be pulled in opposing directions while first mandrel portion 218 and second mandrel portion 219 are gently inserted into first flared region 102 and second flared region 106, respectively. First flared region and second flared region may be inserted until they are sufficiently engaged and first mandrel portion 218 takes up nearly the entire space within first flared region 102 and second mandrel portion 219 takes up nearly the entire space within second flared region 106, thereby depositing and engaging second graft portion 212 with the interior surface of stent 110. Next, second end 215 of graft tube 216 may be separated from second mandrel portion 219, folded over second flared region 106 and laid upon the outer surface of second flared region 106 and neck region 104, thereby depositing first portion over neck region 104 and second flared region 106. Finally, first end 214 may be separated from first mandrel portion 218, folded over first flared region 102 and laid upon the outer surface of second flared region 106 and neck region 104, thereby depositing third portion over second flared region 106 and neck region 104. It is understood that these steps may be repeated to deposit addition layers.

It is further understood that a three-layer structure may be deposited upon stent 110 in similar manner but resulting in the three-layer structure occurring over first flared region 102, second flared region 106, and/or neck region 104. Specifically, this alternative structure may be achieved by depositing first end 214 of graft tube 216 at a different location along stent 110 and following the same general approach illustrated in FIG. 17A-20B. Depending on the length of graft tube 216, the resulting three-layer structure may span over some or all of first flared region 102, second flared region 106 and/or neck region 104.

In another example, a similar stent-graft assembly may be generated using approaches similar to those described above but first depositing second end 215 over neck region 104, thereby placing third graft portion 213 in direct contact with first flared region 102 and neck region 104. Second graft portion 212 may be deposited on the interior portion of stent 110 but first end 214 will be wrapped around second flared region 106 and rest upon first graft portion 211 in neck region 104. It is understood that this process may start with second mandrel portion entering the stent-graft assembly first.

In yet another example, a similar approach may be used to create stent-graft assembly having one region with four layers of biocompatible material and other regions with two layers of biocompatible material. For example, a first graft portion may be deposited on first flared region 102 by positioning graft tube 216 over an exterior of first flared region 102 such that first end 214 is placed over first flared region 102. Second end 215 may then be folded over flared region 102 and guided through the interior of first flared region 102, neck region 104 and out second flared region 106 to deposit a second graft portion along the interior of stent 110. Second end 215 may then be folded over second flared region 106 and guided over the exterior of stent 110 to first flared region 102, thereby depositing a third graft portion over the exterior of second flared region 106, neck region 104 and first flared region 102. Finally, second end 215 may be folded over first flared region 102 and positioned within the interior portion of first flared region 102, thereby depositing a fourth graft portion over the interior of first flared region 102. It is understood that a similar process may be used to deposit four graft layers over second flared region 106 and two graft layers over neck region 104 and first flared region 102.

Referring now to FIGS. 21A-22D, to securely bond first graft portion 211, second graft portion 212, and third graft portion 213 to stent 110 and one another, pressure and heat may be applied to stent-graft assembly 210 to achieve sintering. As explained above, sintering results in strong, smooth, substantially continuous coating that covers the inner and outer surfaces of the stent. Sintering may be achieved by first covering stent-graft assembly 210 with a flexible sleeve (e.g., flexible clamshell 231 shown in FIG. 21A), applying compressor 232 (shown in FIG. 22A), and/or applying heat. In this manner, the first graft portion, second graft portion, and third graft portion may be bonded to one another through through-wall openings in stent 110. Accordingly, third graft portion and second graft portion may be sintered together and joined.

The flexible sleeve may be tubular and also may be elastic and biocompatible. For example, the flexible sleeve may be flexible clamshell 231 illustrated in FIG. 21A. Flexible clamshell 231 is preferably made from biocompatible silicone but may alternatively be other biocompatible materials having elastic properties. Flexible clamshell 231 is hollow and may have a consistent thickness. Alternatively, flexible clamshell 231 may have varying thickness at different points or in different sections. Flexible clamshell 231 has first end 235 and second end 236 which may come together in a neutral position. Alternatively, in a neutral position, there may exist a longitudinal void between first end 235 and second end 236. Flexible clamshell 231 is designed such that first end 235 and second end 236 may be separated by pulling first end 235 and second end 236 in opposing directions.

Figure 21A:
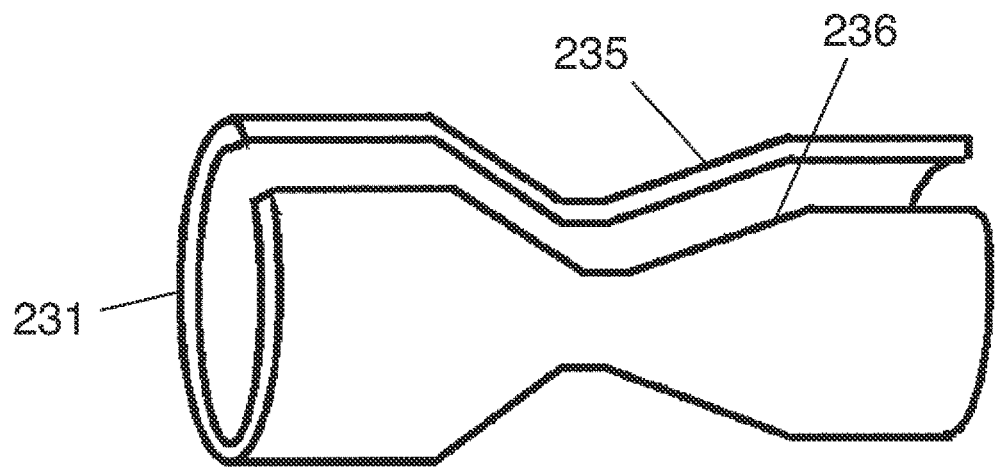
FIGS. 21A-21B illustrate a perspective view of the flexible sleeve and a side view of the flexible sleeve mounted on the stent-graft assembly.
Figure 21B:
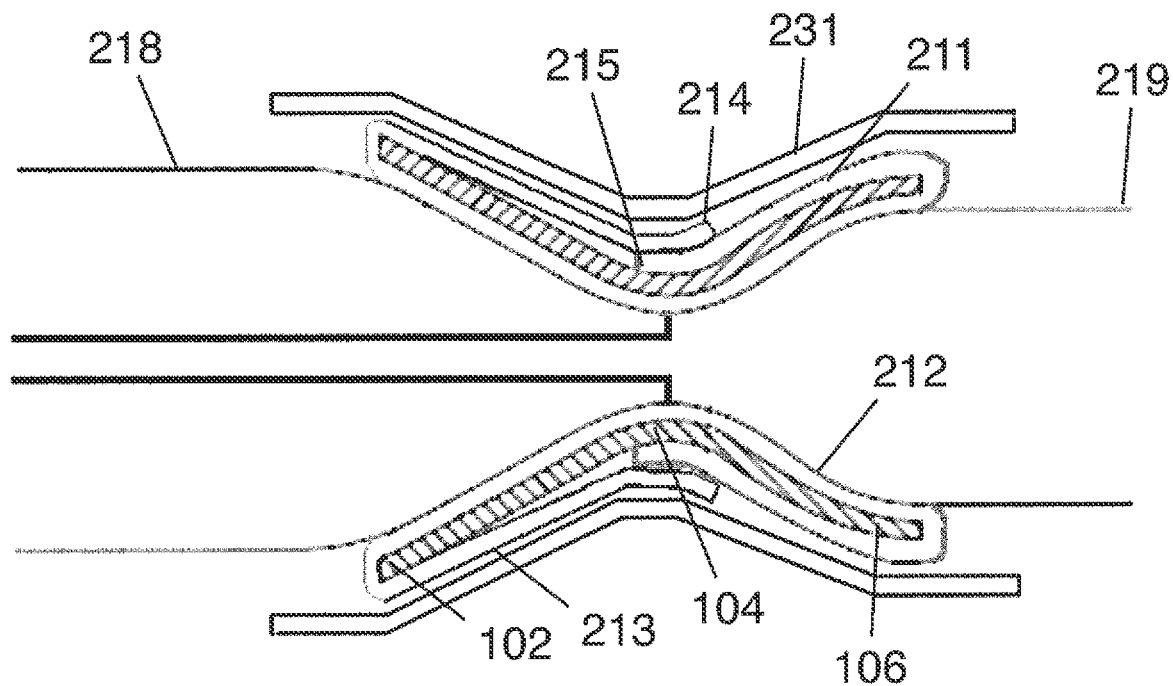

Referring now to FIG. 21B, first end 235 and second end 236 may be pulled in opposing directions to create a longitudinal void such that, while stent-graft assembly 210 is positioned upon mandrel assembly 220, first end 235 and second end 236 may pulled over stent-graft assembly 210. In this manner, flexible clamshell 231 either entirely or nearly entirely covers stent-graft assembly 210. Flexible clamshell 231 may be sized such that flexible clamshell 231 fits tightly over stent-graft assembly 210, as is illustrated in FIG. 21B. It is understood that a thin metallic layer may be deposited over stent-graft assembly 210 prior to covering stent-graft assembly 210 in clamshell 231 such that the thin the metallic layer may be sandwiched between stent-graft assembly 210 and flexible clamshell 231 and may serve as a barrier between stent-graft assembly 210 and flexible clamshell 231. This barrier may help prevent contaminants from clamshell 231 from transferring to stent-graft assembly 210. In one example, the thin metallic layer may be aluminum foil. In other examples, the thin metallic layer may be titanium, tantalum, or stainless steel, though it is understood that other metals or alloys may be used. This process has been observed to enhance the compression and sintering process. Where the stent-graft assembly is wrapped with tape such as TFE or ePTFE tape, the tape may similarly prevent contaminants from transferring to the stent-graft assembly.

Flexible clamshell 231 may be sized such that when positioned over stent-graft assembly 210, flexible clamshell 231 applies a compressive force on stent-graft assembly 210. Flexible clamshell 231 may be sized and configured to optimize the conformance of graft tube 216 to stent 110 to minimize gaps between layers of graft tube 216 adjacent to struts of stent 110. The degree of pressure that flexible clamshell 231 applies to stent-graft assembly 210 may alter the inter nodal distance of the graft material once sintered, described in more detail below. The extent to which flexible clamshell 231 covers, or does not cover, stent-graft assembly 210 also may alter the inter nodal distance. It is understood that inter nodal distance is related to tissue ingrowth and that the compressive force applied by flexible clamshell 231 may be altered to achieve the desired inter nodal distance. Alternatively, any compressive force applied by flexible clamshell 231 may be negligible. Additional compression force on stent-graft assembly 210 may optionally be achieved by first wrapping stent-graft assembly 210 and/or flexible clamshell 231 with tape such as TFE or ePTFE tape. For example, stent-graft assembly 210 covered by flexible clamshell 231 may be placed in a helical winding wrapping machine which tension wraps the stent-graft assembly 210 and flexible clamshell 231 with at least one overlapping layer of tape, explained in more detail above.

Figure 22A:
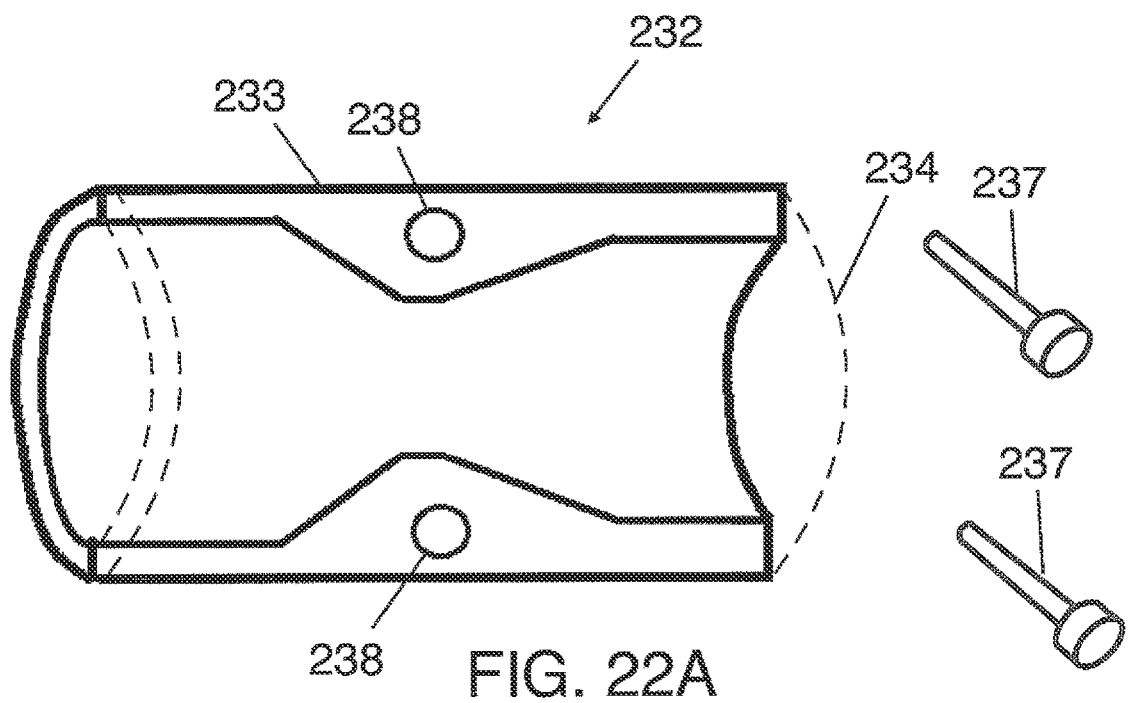
FIGS. 22A-22B illustrate a perspective view of a compression shell and a side view of the flexible sleeve mounted on the flexible sleeve and stent-graft assembly.
Figure 22B:
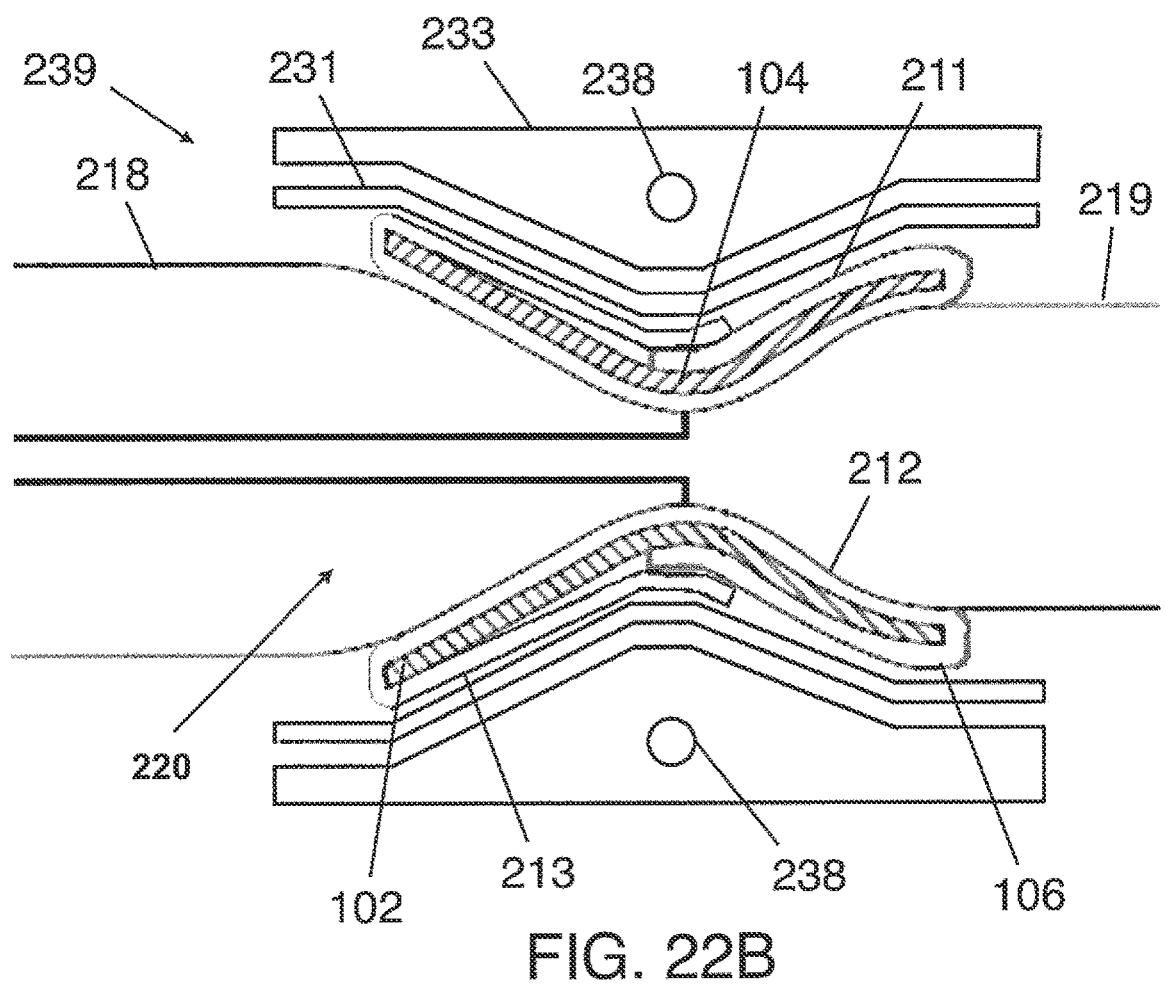

Referring now to FIGS. 22A-22B, compressor 232 is illustrated. Compressor 232 has first half 233 and second half 234 and further includes couplers 237 for removably coupling first half 233 to second half 234. Couplers 237 may involve a screw with a locking nut or any other well-known technique for removably locking two components together. First half 233 and second half 234 may include receiving portions 238 that are sized and configured to receive couplers 237. First half 233 and second half 234 have an interior indentation configured to receive stent-graft assembly 210 covered by flexible clamshell such that the interior indentation of each of first half 233 and second half 234, when removably coupled together, has the shape of stent-graft assembly 210 covered by flexible clamshell 231. Alternatively, the interior indentation of each of first half 233 and second half 234, when removably coupled together, has the shape of the mandrel assembly 220, except with slightly larger radial dimensions.

First half 233 and second half 234 are rigid and preferably are stainless steel though it is understood that first half 233 and second half 234 may be other rigid materials. First half 233 and second half 234 may be designed such that first half 233 and second half 234 are positioned a constant distance from stent-graft assembly 210 when first half 233 and second half 234 are coupled together. Alternatively, the distance from stent-graft assembly 210 or the mandrel assembly 220 may vary at different regions of first half 233 and second half 234. First half 233 and second half 234 may be designed with a wall thickness between an interior surface of first half 233 and second half 234 and an exterior surface of first half 233 and second half 234 that permits a desired degree of heat transfer. For example, first half 233 and second half 234 may have a wall thickness that is thin to increase the amount of heat transfer to the stent-graft assembly. A thinner wall thickness may result in shorter sintering times, which may improve production rates. Further, shorter sintering times lessen the effect of sintering on the transformation temperatures (e.g., Austenitic Finish (Af)) of the Nitinol frame.

Referring now to FIG. 22B, compressor 232 may be attached to clamshell 231 covering stent-graft assembly 210 while stent-graft assembly is mounted upon mandrel assembly 220. Specifically, first half 233 may be positioned over a first half portion of stent-graft assembly 210 and clamshell 231 and second half 234 may be positioned over a second half portion of clamshell 231 and stent-graft assembly 210 such that first half 233 and second half 234 entirely or nearly entirely cover flexible clamshell 231. Once receiving portions 238 of first half 233 and second half 234 are aligned, couplers 237 may be inserted into receiving portions 238 to removably couple first half 233 to second half 234 over clamshell 231. Couplers 237 may be tightened to increase the compressive force applied to stent-graft assembly 210. It is understood that the compressive force applied by couplers 237 may alter the inter nodal distance of the graft material once sintered. It is further understood that couplers 237 may be tightened to a certain degree to achieve a desired inter nodal distance.

Upon coupling first half 233 to second half 234 around flexible clamshell 231, compressor 232 will have been positioned over flexible clamshell 231, flexible clamshell 231 will have been positioned over stent-graft assembly 210, and stent-graft assembly 210 will have been positioned over mandrel assembly 220, as is illustrated in FIG. 22B, forming sintering assembly 239. Upon coupling first half 233 to second half 234, compressor 232 applies a compressive force upon flexible clamshell 231 and stent-graft assembly 210, thereby compressing stent-graft assembly 210 against mandrel assembly 220. Flexible clamshell 231, due to its elastic properties, may facilitate even distribution of compressive force against stent-graft assembly 210. As is shown in FIG. 1, stent 110 may comprise a plurality of through-wall openings. The force exerted by wrapping tape and/or compressor 232 compresses stent-graft assembly 210 against mandrel assembly 220, thereby causing the graft layers to come into intimate contact through interstices of stent 110.

It may be desirable for compressor 232 to apply uniform compressive force. Alternatively, it may be desirable to vary the compressive force applied to stent-graft assembly 210 at certain points along stent-graft assembly 210. For example, flexible clamshell 231 may have varying thickness and/or length, permitting compressor 232 to distribute varying degrees of compressive force upon stent-graft assembly according to the wall thickness and geometry of flexible clamshell 231. Additionally, the distance from the interior walls to the surface of stent-graft assembly 210 may vary at certain points along first half 233 and/or second half 234. For example, a region of an interior wall of first half 233 having a distance to stent-graft assembly 210 less than the rest of first half 233 may apply a greater compression force on stent-graft assembly 210. Varying compressive force applied to stent-graft assembly 210 may reduce or increase conformance between first graft portion 211, second graft portion 212 and third graft portion 213. In an alternative embodiment, compressor 232 may be designed such that it only applies a compression force at neck region 104.

To form a monolithic layer of biocompatible material, first graft portion 211, second graft portion 212, and third graft portion 213 of graft tube 216 may be securely bonded together by applying heat to sintering assembly 239. For example, sintering assembly 239 may be heated by placing sintering assembly 239 into a radiant heat furnace, which may be preheated. Sintering may be performed as discussed in more detail above. The heated assembly may then be allowed to cool for a period of time sufficient to permit manual handling of the assembly. After cooling, first half 233 and second half 234 of compressor 232 may be decoupled and removed from flexible clamshell 231. Next, helical wrap, if any, may be unwound and discarded. Flexible clamshell 231 may be removed and encapsulated stent may then be concentrically rotated about the axis of the mandrel to release any adhesion between the second graft portion 212 and mandrel assembly 220. The encapsulated stent, still on mandrel assembly 220, may then be placed into a laser-trimming fixture to trim excess graft materials away, in any. In addition, the encapsulated stent may be trimmed at various locations along the stent such as near one of the stent ends to permit coupling to delivery device.

The resulting structure shown in FIGS. 16A-16D and created using the approach described with respect to FIGS. 17A-22B is beneficial in that biocompatible material does not terminate at either end of stent-graft assembly 210 but instead terminates at neck region 104 of stent 110. The inventors have discovered that biocompatible material that extends beyond a stent at either end is known to result in thrombus formation when implanted and could also cause interference with attachment to a delivery catheter. The reduction in graft overhang at the edges also improves fluid dynamics at the inlet and outlet of the encapsulated stent. As an added benefit, the resulting triple-layer structure at neck region 104 has been observed by the inventors to further inhibit tissue ingrowth. It is understood that the foregoing method described with respect to FIGS. 17A-22B helps prevent gaps between biocompatible layers, which might result in extensive tissue ingrowth, and also helps minimize microscopic surface thinning defects (MSTDs), which could result in attracting platelet thrombi. Applicants understand that the approach described with respect to FIGS. 17A-22B provides a high yield and highly reproducible manufacturing process.

Applicants have further observed that heating sintering assembly 239 including a flexible clamshell comprised of silicone, as described herein, results in small fragments and/or molecular portions of silicone being deposited upon graft tube 216 and/or becoming impregnated in graft tube 216. It has been observed by the Applicant that the fragments and/or molecular portions of silicone deposited on and/or impregnated in graft tube 216 may further reduce tissue ingrowth when the encapsulated stent is implanted.

Figures 23A, 23B, 23C:
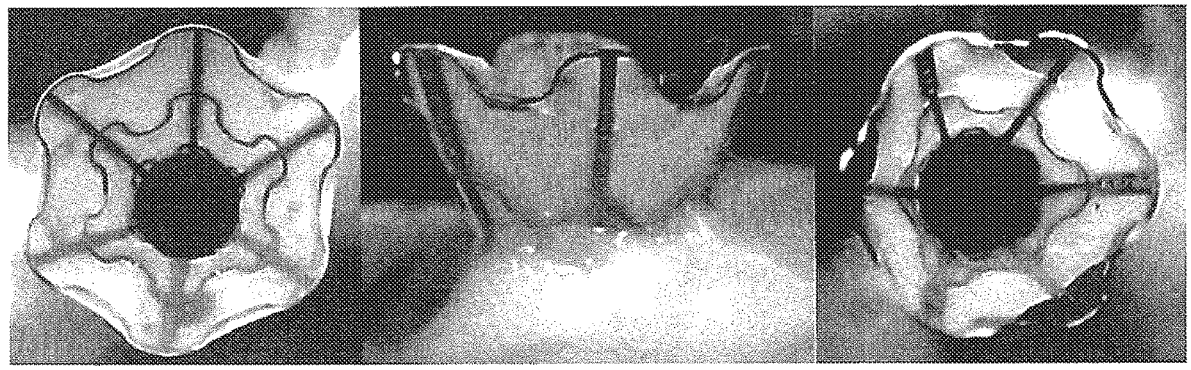
FIGS. 23A-23C illustrate images of an encapsulated stent generated using the approaching shown in FIGS. 17A-22B implanted in an animal subject.

Referring now to FIGS. 23A-C the encapsulated stent generated using the approach described above with respect to FIGS. 17A-22B is shown implanted in the atrial septum of an animal subject. Specifically, FIG. 23A shows the first flared region of the encapsulated stent, FIG. 23B shows the neck region of the encapsulated stent and the second flared region, and FIG. 23C illustrates the second flared region of the encapsulated stent.

While various illustrative embodiments of the invention are described above, it will be apparent to one skilled in the art that various changes and modifications may be made therein without departing from the invention. For example, the assembly mandrels described herein may include additional or fewer components of various sizes and composition. Furthermore, while stent encapsulation is described herein, it is understood that the same procedures may be used to encapsulate any other bio-compatible material. The appended claims are intended to cover all such changes and modifications that fall within the true spirit and scope of the invention.

What is claimed is:

1. A stent-graft assembly comprising:
    an expandable stent comprising a first flared region, a neck region, and a second flared region, the neck region positioned between the first flared region and the second flared region; and
    a continuous biocompatible graft-tube covering the expandable stent, the continuous biocompatible graft tube comprising a first end and a second end, and first, second, and third portions, the first end of the biocompatible graft tube being an end of the first graft portion and the second end of the biocompatible graft tube being an end of the third graft portion, the first graft portion deposited on the neck region and the second flared region of the expandable stent, the second graft portion deposited along an interior surface of the expandable stent and adjacent to the first graft portion and the third graft portion, and the third graft portion deposited along the first flared region and the neck region of the expandable stent, such that:
        the first flared region is covered by two layers of biocompatible material comprising the second graft portion and the third graft portion,
        the neck region is covered by three layers of biocompatible material comprising the first graft portion, the second graft portion, and the third graft portion, and
        the second flared region is covered by two layers of biocompatible material comprising the second graft portion and the first graft portion.

2. The stent-graft assembly of claim 1, wherein the first, second, and third portions of biocompatible graft tube become sintered together into a monolithic layer of graft material upon application of heat, thereby forming an encapsulated stent-graft.

3. The stent-graft assembly of claim 2, wherein the expandable stent comprises through-wall openings such that the application of heat causes the first, second, and third portions to bond to one another through the through-wall openings.

4. The stent-graft assembly of claim 2, wherein the encapsulated stent-graft is configured to transition from a compressed state to an expanded state.

5. The stent-graft assembly of claim 4, wherein the encapsulated stent-graft is configured to transition from the compressed state to an expanded state using an inflatable balloon.

6. A stent-graft assembly comprising:
    an expandable stent having an exterior, a lumen and a first length that includes a first region and first end, a second region and a second end, and a middle region positioned between the first region and the second region; and
    a biocompatible graft-tube having a second length greater than twice the first length, the second length having first, second, and third portions, wherein the first portion extends from the first end of the first region, through the middle region and to the second end of the second region, the second portion is continuously joined to the first portion at the first end and extends from the first end and into the middle region, and the third portion is continuously joined to the second portion at the second end and extends along the second region and into the middle region, such that the second and third portions overlap and are joined to one another.

7. The stent-graft assembly of claim 6, wherein the second and third portions of the biocompatible graft tube are sintered together upon application of heat.

8. The stent-graft assembly of claim 7, wherein the expandable stent comprises through-wall openings such that the first, second, and third portions bond to one another through the through-wall openings upon application of heat to form an encapsulated stent-graft.

9. The stent-graft assembly of claim 8, wherein the encapsulated stent-graft is configured to transition from a compressed state to an expanded state.

10. The stent-graft assembly of claim 8, wherein the encapsulated stent-graft is configured to transition from the compressed state to an expanded state using an inflatable balloon.

11. The stent-graft assembly of claim 6, wherein at least one of the first region and the second region flares outwardly at the first end or the second end, respectively, in an expanded state.

12. The stent-graft assembly of claim 11, wherein both the first region and the second region flare outwardly in the expanded state.

13. The stent-graft assembly of claim 12, wherein the stent-graft assembly forms an hourglass shape in the expanded state.

14. The stent-graft assembly of claim 6, wherein the second and third portions of the biocompatible graft-tube overlap and are joined to one another in the middle region.

15. A stent-graft assembly comprising:
an expandable stent having a first region having a first end, a second region having a second end, and a middle region disposed between the first region and the second region; and
a biocompatible graft-tube having a first portion, a second portion, and a middle portion disposed between the first portion and the second portion, wherein the first portion extends along the expandable stent from the middle region to the first end, the middle portion extends along the expandable stent from the first end to the second end, and the second portion extends along the expandable stent from the second end to the middle region.

16. The stent-graft assembly of claim 15, wherein at least one of the first region and the second region flares outwardly at the first end or the second end, respectively, in an expanded state.

17. The stent-graft assembly of claim 16, wherein both the first region and the second region flare outwardly in the expanded state.

18. The stent-graft assembly of claim 17, wherein the stent-graft assembly forms an hourglass shape in the expanded state.

19. The stent-graft assembly of claim 15, wherein the first portion and the second portion of the biocompatible graft-tube overlap.

20. The stent-graft assembly of claim 19, wherein the first portion and the second portion of the biocompatible graft-tube overlap at the middle region of the expandable stent.

21. The stent-graft assembly of claim 15, wherein the first, second, and middle portions of biocompatible graft-tube become sintered together into a monolithic layer of graft material upon application of heat, thereby forming an encapsulated stent-graft.

22. The stent-graft assembly of claim 21, wherein the expandable stent comprises through-wall openings such that the application of heat causes the first, second, and middle portions to bond to one another through the through-wall openings.

23. The stent-graft assembly of claim 21, wherein the encapsulated stent-graft is configured to transition from a compressed state to an expanded state.

24. The stent-graft assembly of claim 23, wherein the encapsulated stent-graft is configured to transition from the compressed state to an expanded state using an inflatable balloon.

* * * * *